(12) United States Patent
Taylor et al.

(10) Patent No.: US 9,492,062 B2
(45) Date of Patent: Nov. 15, 2016

(54) VISUAL INSUFFLATION PORT

(71) Applicant: Applied Medical Resources Corporation, Rancho Santa Margarita, CA (US)

(72) Inventors: Scott V. Taylor, Rancho Santa Margarita, CA (US); Paul W. Balschweit, Corona, CA (US); Jeremy J. Albrecht, Rancho Santa Margarita, CA (US); Gary M. Johnson, Rancho Santa Margarita, CA (US); Said Hilal, Rancho Santa Margarita, CA (US); Zoran Falkenstein, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 13/964,735

(22) Filed: Aug. 12, 2013

(65) Prior Publication Data

US 2013/0331731 A1    Dec. 12, 2013

Related U.S. Application Data

(63) Continuation of application No. 11/868,883, filed on Oct. 8, 2007, now Pat. No. 8,517,977.

(60) Provisional application No. 60/828,529, filed on Oct. 6, 2006.

(51) Int. Cl.
*A61B 1/00* (2006.01)
*A61B 1/015* (2006.01)
(Continued)

(52) U.S. Cl.
CPC ......... *A61B 1/00154* (2013.01); *A61B 1/0008* (2013.01); *A61B 1/015* (2013.01);
(Continued)

(58) Field of Classification Search
CPC ............. A61B 1/015; A61B 17/3474; A61B 2017/3441; A61B 2017/3456; A61M 13/00; A61M 13/003
USPC ............................................... 604/26, 167.03
See application file for complete search history.

(56) References Cited

U.S. PATENT DOCUMENTS

RE682 E     4/1859  Peale
184,573 A   11/1876 Becker
(Continued)

FOREIGN PATENT DOCUMENTS

BE    1 006 811    12/1994
CA    2 170 841     9/1997
(Continued)

OTHER PUBLICATIONS

U.S. Appl. No. 10/745,262; filed Dec. 23, 2003; Title: "Catheter With Conduit Traversing Tip" (abandoned).
(Continued)

*Primary Examiner* — Kami A Bosworth
(74) *Attorney, Agent, or Firm* — Rimas T. Lukas

(57) ABSTRACT

A visual insufflation obturator is provided. The obturator includes seals, valves, screens and/or various other tip features to eliminate the ingress of fluids, matter and/or gas that can disrupt the visual field of the laparoscope disposed within the obturator. The obturator provides additional features such as lens and anti-fog features to further increase visibility of the scope, efficiently insufflate the patient and ultimately provide an access channel into the insufflated abdomen once the visual insufflation obturator is removed.

19 Claims, 22 Drawing Sheets

(51) Int. Cl.
*A61B 1/12* (2006.01)
*A61B 1/313* (2006.01)
*A61B 17/34* (2006.01)
*A61M 13/00* (2006.01)
*A61B 17/00* (2006.01)

(52) U.S. Cl.
CPC ............ *A61B 1/127* (2013.01); *A61B 1/3132* (2013.01); *A61B 17/3474* (2013.01); *A61M 13/003* (2013.01); *A61B 90/361* (2016.02); *A61B 2017/00907* (2013.01); *A61B 2017/346* (2013.01); *A61B 2017/3441* (2013.01); *A61B 2017/3454* (2013.01); *A61B 2017/3456* (2013.01)

(56) References Cited

U.S. PATENT DOCUMENTS

| | | |
|---|---|---|
| 224,513 A | 2/1880 | Burdon |
| 396,754 A | 1/1889 | Mayfield |
| 764,322 A | 7/1904 | Wiegand |
| 1,147,408 A | 7/1915 | Kelis |
| 1,672,258 A | 6/1928 | Hippenmeyer |
| 1,727,495 A | 9/1929 | Wappler |
| 1,845,727 A | 2/1932 | Slaughter |
| 2,102,274 A | 12/1937 | Larimore |
| 2,189,343 A | 2/1940 | Fritz |
| 2,301,338 A | 11/1942 | Smith |
| 2,434,594 A | 1/1948 | Schultz |
| 2,441,143 A | 5/1948 | Gracey |
| 2,646,701 A | 7/1953 | Lietin |
| 2,699,770 A | 1/1955 | Fourestier et al. |
| 2,764,148 A | 9/1956 | Sheldon |
| 2,764,149 A | 9/1956 | Sheldon |
| 2,769,355 A | 11/1956 | Henry |
| 2,877,368 A | 3/1959 | Sheldon |
| 2,932,294 A | 4/1960 | Fourestier et al. |
| 3,005,468 A | 10/1961 | Erwin et al. |
| 3,021,834 A | 2/1962 | Sheldon |
| 3,033,226 A | 5/1962 | Allen |
| 3,042,022 A | 7/1962 | Sheldon |
| 3,224,320 A | 12/1965 | Knudsen |
| 3,277,922 A | 10/1966 | Eisel |
| 3,279,460 A | 10/1966 | Sheldon |
| 3,357,433 A | 12/1967 | Fourestier et al. |
| 3,385,553 A | 5/1968 | Braun |
| 3,417,745 A | 12/1968 | Sheldon |
| 3,437,747 A | 4/1969 | Sheldon |
| 3,459,189 A | 8/1969 | Alley et al. |
| 3,556,085 A | 1/1971 | Takahashi |
| 3,613,684 A | 10/1971 | Sheridan |
| 3,653,338 A | 4/1972 | Sauey |
| 3,791,379 A | 2/1974 | Storz |
| 3,817,251 A | 6/1974 | Hasson |
| 3,821,956 A | 7/1974 | Gordhamer |
| 3,870,036 A | 3/1975 | Fiore |
| 3,961,621 A | 6/1976 | Northeved |
| 3,971,385 A | 7/1976 | Corbett |
| 3,994,287 A | 11/1976 | Turp |
| 3,994,301 A | 11/1976 | Agris |
| 4,028,987 A | 6/1977 | Wilson |
| 207,932 A | 9/1978 | Alvord |
| 4,112,932 A | 9/1978 | Chiulli |
| 4,126,291 A | 11/1978 | Gilbert et al. |
| 4,150,929 A | 4/1979 | Brandt |
| 4,168,882 A | 9/1979 | Hopkins |
| 4,180,068 A | 12/1979 | Jacobsen et al. |
| 4,191,191 A | 3/1980 | Auburn |
| 4,222,375 A | 9/1980 | Martinez |
| 4,248,214 A | 2/1981 | Hannah et al. |
| 4,254,762 A | 3/1981 | Yoon |
| 4,269,192 A | 5/1981 | Matsuo |
| 4,274,771 A | 6/1981 | Nishimura |
| 4,285,618 A | 8/1981 | Shanley |
| 4,299,230 A | 11/1981 | Kubota |
| 4,311,138 A | 1/1982 | Sugarman |
| 4,319,563 A | 3/1982 | Kubota |
| 4,356,826 A | 11/1982 | Kubota |
| 4,386,179 A | 5/1983 | Sterling |
| 4,414,966 A | 11/1983 | Stednitz |
| 4,429,856 A | 2/1984 | Jackson |
| 4,436,519 A | 3/1984 | O'Neill |
| 4,493,444 A | 1/1985 | Del Bon et al. |
| 4,498,902 A | 2/1985 | Ash et al. |
| 4,524,805 A | 6/1985 | Hoffman |
| 4,535,773 A | 8/1985 | Yoon |
| 4,535,808 A | 8/1985 | Johanson et al. |
| 4,537,593 A | 8/1985 | Alchas |
| 4,567,882 A | 2/1986 | Heller |
| 4,601,710 A | 7/1986 | Moll |
| 4,607,619 A | 8/1986 | Seike et al. |
| 4,750,877 A | 6/1988 | McFarlane |
| 4,762,130 A | 8/1988 | Fogarty et al. |
| 4,779,613 A | 10/1988 | Hashiguchi et al. |
| 4,803,999 A | 2/1989 | Liegner |
| 4,813,400 A | 3/1989 | Washizuka et al. |
| 4,850,393 A | 7/1989 | Lashomb |
| 4,895,431 A | 1/1990 | Tsujiuchi et al. |
| 4,901,142 A | 2/1990 | Ikuno et al. |
| 4,956,143 A | 9/1990 | McFarlane |
| 4,959,067 A | 9/1990 | Muller |
| 4,972,827 A | 11/1990 | Kishi et al. |
| 4,978,350 A | 12/1990 | Wagenknecht |
| 5,017,057 A | 5/1991 | Kryger |
| 5,030,210 A | 7/1991 | Alchas |
| 5,041,100 A | 8/1991 | Rowland et al. |
| 5,057,082 A | 10/1991 | Burchette, Jr. |
| 5,066,288 A | 11/1991 | Deniega et al. |
| 5,098,379 A | 3/1992 | Conway |
| 5,098,388 A | 3/1992 | Kulkashi et al. |
| 5,104,316 A | 4/1992 | Mc Spadden |
| 5,104,388 A | 4/1992 | Quackenbush |
| 5,104,389 A | 4/1992 | Deem et al. |
| 5,114,407 A | 5/1992 | Burbank |
| 5,116,547 A | 5/1992 | Tsukahara et al. |
| 5,137,509 A * | 8/1992 | Freitas ........................ 604/26 |
| 5,144,942 A | 9/1992 | Decarie et al. |
| 5,147,376 A | 9/1992 | Pianetti |
| 5,159,920 A | 11/1992 | Condon et al. |
| 5,163,941 A | 11/1992 | Garth et al. |
| 5,178,186 A | 1/1993 | Levasseur |
| 5,186,972 A | 2/1993 | Williams et al. |
| 5,197,955 A | 3/1993 | Stephens et al. |
| 5,207,656 A | 5/1993 | Kranys |
| 5,217,441 A | 6/1993 | Shichman |
| 5,221,163 A | 6/1993 | Nishimura |
| 5,240,397 A | 8/1993 | Fay et al. |
| 5,246,425 A | 9/1993 | Hunsberger et al. |
| 5,250,068 A | 10/1993 | Ideguchi et al. |
| 5,256,149 A | 10/1993 | Banik et al. |
| 5,258,003 A | 11/1993 | Ciaglia |
| 5,269,316 A | 12/1993 | Spitalny |
| 5,271,380 A | 12/1993 | Riek et al. |
| 5,279,567 A | 1/1994 | Ciaglia et al. |
| 5,288,290 A | 2/1994 | Brody |
| 5,290,276 A | 3/1994 | Sewell |
| 5,290,585 A | 3/1994 | Elton |
| 5,300,033 A | 4/1994 | Miller |
| 5,334,150 A | 8/1994 | Kaali |
| 5,342,382 A | 8/1994 | Brinkerhoff |
| 5,350,364 A | 9/1994 | Stephens et al. |
| 5,370,624 A | 12/1994 | Edwards et al. |
| 5,372,588 A | 12/1994 | Farley |
| 5,374,253 A | 12/1994 | Burns, Sr. et al. |
| 5,380,291 A | 1/1995 | Kaali |
| 5,387,197 A | 2/1995 | Smith |
| 5,389,077 A | 2/1995 | Melinyshyn et al. |
| 5,391,153 A | 2/1995 | Haber et al. |
| 5,391,248 A | 2/1995 | Brain |
| 5,392,766 A | 2/1995 | Masterson et al. |
| 5,405,328 A | 4/1995 | Vidal et al. |
| 5,407,427 A | 4/1995 | Zhu et al. |
| 5,431,151 A | 7/1995 | Riek et al. |
| 5,441,041 A | 8/1995 | Sauer et al. |

(56) References Cited

U.S. PATENT DOCUMENTS

| | | |
|---|---|---|
| 5,443,484 A | 8/1995 | Kirsch et al. |
| 5,445,615 A | 8/1995 | Yoon et al. |
| 5,454,791 A | 10/1995 | Tovey et al. |
| 5,474,541 A * | 12/1995 | Ritsky et al. ............... 604/213 |
| 5,480,410 A | 1/1996 | Cuschieri et al. |
| 5,510,065 A | 4/1996 | McFarlane |
| 5,540,711 A | 7/1996 | Kieturakis et al. |
| 5,542,845 A | 8/1996 | Jenkins |
| 5,549,546 A | 8/1996 | Schneider et al. |
| 5,551,947 A | 9/1996 | Kaali |
| 5,562,696 A | 10/1996 | Nobles et al. |
| 5,569,291 A | 10/1996 | Privitera |
| 5,569,292 A | 10/1996 | Scwemberger et al. |
| 5,577,993 A | 11/1996 | Zhu et al. |
| 5,591,186 A | 1/1997 | Wurster et al. |
| 5,591,192 A | 1/1997 | Privitera et al. |
| 5,593,402 A | 1/1997 | Patrick |
| 5,603,720 A | 2/1997 | Kieturakis |
| 5,609,562 A | 3/1997 | Kaali |
| 5,609,604 A | 3/1997 | Schwemberger et al. |
| 5,613,954 A | 3/1997 | Nelson et al. |
| 5,622,462 A | 4/1997 | Gakhar et al. |
| 5,630,805 A | 5/1997 | Ternamian |
| 5,634,908 A | 6/1997 | Loomas |
| 5,658,236 A | 8/1997 | Sauer |
| 5,662,615 A | 9/1997 | Blake, III |
| 5,662,673 A | 9/1997 | Kieturakis |
| 5,676,611 A | 10/1997 | Foster |
| 5,685,820 A | 11/1997 | Riek et al. |
| 5,695,462 A | 12/1997 | Sutcu et al. |
| 5,697,947 A | 12/1997 | Wolf |
| 5,720,730 A | 2/1998 | Blake, III |
| 5,720,761 A | 2/1998 | Kaali |
| 5,735,867 A | 4/1998 | Golser et al. |
| 5,738,628 A | 4/1998 | Sierocuk |
| 5,743,881 A | 4/1998 | Demco |
| 5,746,734 A | 5/1998 | Dormandy, Jr. et al. |
| 5,752,970 A | 5/1998 | Yoon et al. |
| 5,759,185 A | 6/1998 | Grinberg |
| 5,779,697 A | 7/1998 | Glowa et al. |
| 5,785,693 A | 7/1998 | Haining |
| 5,792,112 A | 8/1998 | Hart et al. |
| 5,797,888 A | 8/1998 | Yoon et al. |
| 5,797,944 A | 8/1998 | Nobles et al. |
| 5,817,061 A | 10/1998 | Goodwin et al. |
| 5,817,062 A | 10/1998 | Flom et al. |
| 5,836,957 A | 11/1998 | Schulz |
| 5,842,971 A | 12/1998 | Yoon |
| 5,860,996 A | 1/1999 | Urban et al. |
| 5,865,809 A | 2/1999 | Moenning et al. |
| 5,871,474 A | 2/1999 | Hermann et al. |
| 5,876,202 A | 3/1999 | Berlin |
| 5,884,639 A | 3/1999 | Chen |
| 5,891,013 A | 4/1999 | Thompson |
| 5,893,865 A | 4/1999 | Swindle |
| 5,904,699 A | 5/1999 | Schwemberger et al. |
| 5,913,818 A | 6/1999 | Co et al. |
| 5,922,351 A | 7/1999 | Daher |
| 5,924,452 A | 7/1999 | Szpara et al. |
| 5,941,852 A | 8/1999 | Dunlap et al. |
| 5,957,884 A | 9/1999 | Hooven |
| 5,957,888 A | 9/1999 | Hinchliffe |
| 5,968,060 A | 10/1999 | Kellogg |
| 5,976,079 A | 11/1999 | Volz et al. |
| 5,976,168 A | 11/1999 | Chin |
| 5,980,809 A | 11/1999 | Crain et al. |
| 5,984,941 A | 11/1999 | Wilson |
| 6,001,084 A | 12/1999 | Riek |
| 6,007,481 A | 12/1999 | Riek et al. |
| 6,007,544 A | 12/1999 | Kim |
| 6,019,776 A | 2/2000 | Preissman |
| 6,024,551 A | 2/2000 | Yamaguchi |
| 6,030,406 A | 2/2000 | Davis |
| 6,043,310 A | 3/2000 | Liu et al. |
| 6,053,194 A | 4/2000 | Nelson et al. |
| 6,068,637 A | 5/2000 | Popov et al. |
| 6,077,481 A | 6/2000 | Ichida et al. |
| 6,092,551 A | 7/2000 | Bennett |
| 6,168,355 B1 | 1/2001 | Wardell |
| 6,179,528 B1 | 1/2001 | Wardell |
| 6,203,559 B1 | 3/2001 | Davis |
| 6,203,745 B1 | 3/2001 | Wachsmann et al. |
| 6,221,061 B1 | 4/2001 | Engelson et al. |
| 6,228,059 B1 | 5/2001 | Astarita |
| 6,228,063 B1 | 5/2001 | Aboul-Hosn |
| 6,270,484 B1 | 8/2001 | Yoon |
| 6,302,873 B1 | 10/2001 | Moenning |
| 6,319,266 B1 | 11/2001 | Stellon |
| 6,346,074 B1 | 2/2002 | Roth |
| 6,355,014 B1 | 3/2002 | Zadno-Azizi et al. |
| 6,387,043 B1 | 5/2002 | Yoon |
| 6,462,111 B1 | 10/2002 | Singh et al. |
| 6,468,228 B1 | 10/2002 | Topel et al. |
| 6,478,806 B2 | 11/2002 | McFarlane |
| 6,508,759 B1 | 1/2003 | Taylor et al. |
| 6,520,939 B2 | 2/2003 | Lafontaine |
| 6,656,160 B1 | 12/2003 | Taylor et al. |
| 6,656,198 B2 | 12/2003 | Tsonton et al. |
| 6,685,630 B2 | 2/2004 | Sauer et al. |
| 6,764,107 B1 | 7/2004 | Obahi et al. |
| 6,770,731 B2 | 8/2004 | Mason et al. |
| 6,835,201 B2 | 12/2004 | O'Heeron |
| 6,884,253 B1 | 4/2005 | McFarlane |
| 6,887,194 B2 | 5/2005 | Hart et al. |
| 6,902,541 B2 | 6/2005 | McNally et al. |
| 6,939,296 B2 | 9/2005 | Ewers et al. |
| 7,008,979 B2 | 3/2006 | Schottman et al. |
| 7,037,303 B2 | 5/2006 | Beaufore et al. |
| 7,056,294 B2 | 6/2006 | Khairkhahan et al. |
| 7,056,329 B2 | 6/2006 | Kerr |
| 7,070,586 B2 | 7/2006 | Hart et al. |
| 7,182,752 B2 | 2/2007 | Stubbs |
| 7,344,519 B2 | 3/2008 | Wing et al. |
| 7,370,709 B2 | 5/2008 | Williamson, Jr. |
| 7,470,255 B2 | 12/2008 | Stearns et al. |
| 7,563,250 B2 | 7/2009 | Wenchell |
| 7,686,823 B2 | 3/2010 | Pingleton et al. |
| 7,708,713 B2 | 5/2010 | Albrecht et al. |
| 7,758,603 B2 | 7/2010 | Taylor et al. |
| 7,794,644 B2 | 9/2010 | Taylor et al. |
| 7,811,253 B2 | 10/2010 | Hart et al. |
| 7,942,862 B2 | 5/2011 | Hart et al. |
| 7,947,058 B2 | 5/2011 | Kahle et al. |
| 8,007,477 B2 | 8/2011 | Johnson et al. |
| 8,028,395 B2 | 10/2011 | Taylor et al. |
| 8,075,530 B2 | 12/2011 | Taylor et al. |
| 8,105,285 B2 | 1/2012 | Hart et al. |
| 8,128,590 B2 | 3/2012 | Albrecht et al. |
| 8,152,828 B2 | 4/2012 | Taylor et al. |
| 8,267,952 B2 | 9/2012 | Kahle et al. |
| 8,282,663 B2 | 10/2012 | Smith |
| 8,292,853 B2 | 10/2012 | Hart et al. |
| 8,317,815 B2 | 11/2012 | Mastri et al. |
| 8,377,090 B2 | 2/2013 | Taylor et al. |
| 8,382,663 B2 | 2/2013 | Taylor |
| 2002/0013597 A1 | 1/2002 | McFarlane |
| 2002/0026207 A1 | 2/2002 | Stellon et al. |
| 2002/0133188 A1 | 9/2002 | O'Heeron et al. |
| 2002/0183715 A1 | 12/2002 | Mantell et al. |
| 2002/0183775 A1 | 12/2002 | Tsonton et al. |
| 2003/0023201 A1 | 1/2003 | Aboul-Hosn |
| 2003/0032755 A1 | 2/2003 | Gorny et al. |
| 2003/0059263 A1 | 3/2003 | Chen |
| 2003/0187471 A1 | 10/2003 | Cooper |
| 2004/0015185 A1 | 1/2004 | Ewers et al. |
| 2004/0082969 A1 | 4/2004 | Kerr |
| 2004/0093000 A1 | 5/2004 | Kerr |
| 2004/0093018 A1 | 5/2004 | Johnson et al. |
| 2004/0106942 A1 | 6/2004 | Taylor et al. |
| 2004/0108623 A1 | 6/2004 | Deeter et al. |
| 2004/0167559 A1 | 8/2004 | Taylor et al. |
| 2004/0199127 A1 | 10/2004 | Jensen et al. |
| 2004/0204671 A1 | 10/2004 | Stubbs et al. |
| 2004/0230155 A1 | 11/2004 | Blanco et al. |

(56) References Cited

U.S. PATENT DOCUMENTS

| | | |
|---|---|---|
| 2004/0230217 A1 | 11/2004 | O'Heeron |
| 2004/0254517 A1 | 12/2004 | Quiroz-Mercado et al. |
| 2005/0033237 A1 | 2/2005 | Fentress et al. |
| 2005/0033246 A1 | 2/2005 | Ahlberg et al. |
| 2005/0038466 A1 | 2/2005 | O'Heeron et al. |
| 2005/0059865 A1 | 3/2005 | Kahle |
| 2005/0065543 A1 | 3/2005 | Kahle et al. |
| 2005/0107803 A1 | 5/2005 | Guanche |
| 2005/0107816 A1 | 5/2005 | Pingleton et al. |
| 2005/0113533 A1 | 5/2005 | Shaikh et al. |
| 2005/0149094 A1 | 7/2005 | Kasahara et al. |
| 2005/0149096 A1 | 7/2005 | Hilal et al. |
| 2005/0159711 A1 | 7/2005 | Kathrani et al. |
| 2005/0216028 A1 | 9/2005 | Hart et al. |
| 2005/0227610 A1 | 10/2005 | Zukor et al. |
| 2005/0273133 A1 | 12/2005 | Shluzas et al. |
| 2005/0283122 A1 | 12/2005 | Nordgren |
| 2005/0288622 A1 | 12/2005 | Albrecht et al. |
| 2006/0030755 A1 | 2/2006 | Ewers et al. |
| 2006/0030870 A1 | 2/2006 | Staudner |
| 2006/0041270 A1 | 2/2006 | Lenker et al. |
| 2006/0047284 A1 | 3/2006 | Gresham |
| 2006/0058570 A1 | 3/2006 | Rapach et al. |
| 2006/0074374 A1 | 4/2006 | Gresham |
| 2006/0118189 A1 | 6/2006 | Tekulve et al. |
| 2006/0224174 A1 | 10/2006 | Smith et al. |
| 2006/0264991 A1 | 11/2006 | Johnson |
| 2007/0027453 A1 | 2/2007 | Hart et al. |
| 2007/0075465 A1 | 4/2007 | Taylor et al. |
| 2007/0088277 A1 | 4/2007 | McGinley |
| 2007/0239108 A1 | 10/2007 | Albrecht et al. |
| 2008/0065021 A1 | 3/2008 | Jenkins et al. |
| 2008/0086074 A1 | 4/2008 | Taylor et al. |
| 2008/0086093 A1 | 4/2008 | Steppe et al. |
| 2009/0030375 A1 | 1/2009 | Franer et al. |
| 2009/0137943 A1 | 5/2009 | Stearns et al. |
| 2009/0187079 A1 | 7/2009 | Albrecht et al. |
| 2009/0281500 A1 | 11/2009 | Acosta et al. |
| 2010/0025045 A1 | 2/2010 | Lake et al. |

FOREIGN PATENT DOCUMENTS

| | | |
|---|---|---|
| DE | 0365049 | 12/1922 |
| DE | 1616107 | 4/1971 |
| DE | 2218901 | 10/1973 |
| DE | 2538758 | 3/1977 |
| DE | 2929233 | 1/1980 |
| DE | 2922239 | 12/1980 |
| DE | 4020956 | 1/1991 |
| DE | 4133073 | 4/1992 |
| DE | 4035146 | 5/1992 |
| DE | 4116648 | 11/1992 |
| DE | 29503750 | 4/1995 |
| DE | 29521431 | 4/1997 |
| DE | 19541041 | 5/1997 |
| DE | 19718086 | 11/1998 |
| DE | 19819432 | 11/1999 |
| EP | 0135364 | 3/1985 |
| EP | 0312787 | 4/1989 |
| EP | 0347140 | 12/1989 |
| EP | 0369936 | 5/1990 |
| EP | 0369937 | 5/1990 |
| EP | 0474124 | 3/1992 |
| EP | 0548612 | 6/1993 |
| EP | 0556056 | 8/1993 |
| EP | 0664992 | 8/1995 |
| EP | 0724864 | 8/1996 |
| EP | 1074224 | 2/2001 |
| EP | 1582158 | 10/2005 |
| EP | 2229897 | 9/2010 |
| EP | 2233090 | 9/2010 |
| FR | 1370580 | 8/1964 |
| GB | 2 124 970 | 2/1984 |
| GB | 186 005 | 9/1992 |
| GB | 2 313 316 | 11/1997 |
| JP | 408127661 | 5/1996 |
| JP | 2001-137253 | 5/2001 |
| SU | 0942730 | 7/1982 |
| SU | 1328658 | 8/1987 |
| SU | 1329769 | 8/1987 |
| WO | WO 93/25148 | 12/1993 |
| WO | WO 98/33536 | 2/1994 |
| WO | WO 94/11040 | 5/1994 |
| WO | WO 96/01074 A2 | 1/1996 |
| WO | WO 96/01132 | 1/1996 |
| WO | WO 96/10361 | 4/1996 |
| WO | WO 97/40758 | 11/1997 |
| WO | WO 99/02089 | 1/1999 |
| WO | WO 99/15084 | 4/1999 |
| WO | WO 00/18306 | 4/2000 |
| WO | WO 00/54648 | 9/2000 |
| WO | WO 01/01847 | 1/2001 |
| WO | WO 01/01871 | 1/2001 |
| WO | WO 02/01998 | 1/2002 |
| WO | WO 01/08563 | 2/2002 |
| WO | WO 02/34108 | 5/2002 |
| WO | WO 02/41795 | 5/2002 |
| WO | WO 03/026512 | 4/2003 |
| WO | WO 03/032819 | 4/2003 |
| WO | WO 03/096879 | 11/2003 |
| WO | WO 2004/037097 | 5/2004 |
| WO | WO 2004/093699 | 11/2004 |
| WO | WO 2005/063134 | 7/2005 |
| WO | WO 2007/093957 | 8/2007 |

OTHER PUBLICATIONS

Co-Pending U.S. Appl. No. 12/750,372, filed Mar. 30, 2010, title: "Bladeless Obturator".

Co-Pending U.S. Appl. No. 11/549,872, filed Oct. 16, 2006, title: "Surgical Devices, Systems and Methods Thereof Having Gel Material, Gel Coatings, or Gel Lubricants".

Co-Pending U.S. Appl. No. 13/565,972, filed Aug. 3, 2012, title: "Bladeless Optical Obturator".

Co-Pending U.S. Appl. No. 13/356,260 filed Jan. 23, 2012, title: "Insufflating Optical Surgical Instrument".

Co-Pending U.S. Appl. No. 13/078,750 filed Apr. 1, 2011 title "Surgical Access Apparatus and Method".

Co-Pending U.S. Appl. No. 12/569,652 filed Sep. 29, 2009; title "First-Entry Trocar System".

Co-Pending U.S. Appl. No. 12/359,964 filed Jan. 26, 2009, title: "Insufflating Access System".

Co-Pending U.S. Appl. No. 13/462,330 filed May 2, 2012, title: "Low-Profile Surgical Universal Access Port".

Co-Pending U.S. Appl. No. 13/411,244 filed Mar. 2, 2012, title: "Blunt Tip Obturator".

Co-Pending U.S. Appl. No. 13/586,825 filed Aug. 15, 2012, title: "Blunt Tip Obturator".

Co-Pending U.S. Appl. No. 11/868,883; filed Oct. 8, 2007; Title: "Visual Insufflation Port".

International Bureau of WIPO, International Preliminary Report on Patentability for International Application No. PCT/US04/032346, dated May 20, 2008.

International Bureau of WIPO, International Preliminary Report on Patentability for International Application No. PCT/US2005/022716 mailed Nov. 22, 2005.

International Bureau of WIPO, International Preliminary Report on Patentability for International Application No. PCT/US2006/060013, mailed Apr. 24, 2008.

International Bureau of WIPO, The International Preliminary Report on Patentability for International Application No. PCT/US2009/058792, titled First Entry Trocar System, dated Mar. 29, 2011.

International Bureau of WIPO, The International Preliminary Report on Patentability for International Application No. PCT/US2007/080724, titled "Visual Insufflation Port", dated Apr. 7, 2009,.

International Bureau of WIPO, The International Preliminary Report on Patentability for International Application No. PCT/US2009/32026, titled "Insufflating Access System", dated Jul. 27, 2010.

(56) References Cited

OTHER PUBLICATIONS

International Bureau of WIPO, The International Preliminary Report on Patentability for International Application No. PCT/US2004/000695, titled "Surgical Access Apparatus and Method", dated Jul. 22, 2005.
International Bureau of WIPO, The International Preliminary Report on Patentability for International Application No. PCT/US2004/04883, titled "Surgical Access Apparatus and Method", dated Sep. 9, 2005.
International Searching Authority, International Search Report and Written Opinion for International Application No. PCT/US2004/000695, titled "Surgical Access Apparatus and Method", mailed Jan. 12, 2005.
International Searching Authority, International Search Report and Written Opinion for International Application No. PCT/US2004/04883, titled "Surgical Access Apparatus and Method", mailed Mar. 31, 2005.
International Searching Authority, International Search Report and Written Opinion for International Application No. PCT/US2002/06759, titled "Bladeless Obturator", mailed Jul. 12, 2002.
International Searching Authority, International Search Report and Written Opinion for International Application No. PCT/US2005/022716, titled "Insufflating Optical Surgical Instrument", mailed Nov. 22, 2005.
International Searching Authority, International Search Report and Written Opinion for International Application No. PCT/US04/32346, titled Bladeless Optical Obturator, mailed May 20, 2008.
International Searching Authority, International Search Report and Written Opinion for International Application No. PCT/US2009/32026, titled "Insufflating Access System", mailed Mar. 23, 2009.
International Searching Authority, International Search Report and Written Opinion for International Application No. PCT/US2007/080724, titled "Visual Insufflation Port", mailed Apr. 16, 2008.
International Searching Authority/US, International Search Report and the Written Opinion of the International Searching Authority dated May 27, 2009, for International Application No. PCT/US2009/037863, titled "Instrument Seal with Inverting Shroud", mailed May 27, 2009.
The International Searching Authority, The International Search Report and the Written Opinion for International Application No. PCT/US2009/058792, titled "First Entry Trocar System", mailed Dec. 23, 2009.
International Searching Authority, International Search Report and Written Opinion for International Application No. PCT/US2012/036119, title "Low-Profile Surgical Universal Access Port", mailed Nov. 7, 2012.
European Patent Office, Supplementary European Search Report for European Patent Application No. EP 04 70 1731 based PCT/US2004/000695, titled "Surgical Access European Search Report for European on International Application No. Apparatus and Method", dated Apr. 11, 2007.
European Patent Office, Supplementary European Search Report for European Patent Application No. EP 02706494.8, titled "Bladeless Obturator", dated Jun. 24, 2008.
European Patent Office, Supplementary European Search Report for European Patent Application No. EP 03753017.7, titled "Blunt Tip Obturator", dated Nov. 21, 2008.
European Patent Office, Supplementary European Search Report for European Patent Application No. EP 04712378, titled "Surgical Access Apparatus and Method", dated May 19, 2008.
European Patent Office, Supplementary European Search Report for European Patent Application No. EP 07843973.4, titled "Visual Insufflation Port" dated Oct. 4, 2008.
European Patent Office, Supplementary European Search Report for European Patent Application No. EP 04793965.7, titled "Bladeless Optical Obturator", dated Apr. 16, 2010.
European Patent Office, Supplementary European Search Report for European Patent Application No. EP 11154547.1, titled "Blunt Tip Obturator", dated Mar. 22, 2011.
European Patent Office, European Search Report for European Application No. 11191191.3, titled "Bladeless Obturator" dated Feb. 29, 2012.
European Patent Office, European Search Report for European Application No. 11191179.8, titled "Bladeless Obturator", dated Feb. 21, 2012.
European Patent Office, European Search Report for European Application No. 11191193.9, titled "Bladeless Obturator", dated Mar. 5, 2012.
European Patent Office, European Search Report for European Application No. 11191187.1, titled Bladeless Obturator, dated Feb. 23, 2012.
European Patent Office, European Search Report for European Application No. 11191184.8, titled "Bladeless Obturator", dated Feb. 23, 2012.
European Patent Office, European Search Report for European Application No. 11191189.7, titled "Bladeless Obturator", dated Feb. 24, 2012.
European Patent Office, European Search Report for European Application No. 11191175.6, titled "Bladeless Obturator", dated Feb. 21, 2012.
European Patent Office, European Search Report for European Application No. 047017314, titled "Surgical Access Apparatus and Method", dated Mar. 30, 2007,.
Taut, Inc., ADAPT-Asymmetrical Dilating Access Port, Geneva Illinois.
Karl Storz, The Karl Storz Ternamian EndoTIP (TM) System, date: Aug. 27, 2001.
Karl Storz, ZEROCART Trocar with eccentric tip, Recklinghausen, Germany, date Mar. 7, 2001.
Ethicon Endo-Surgery, Inc., ENDOPATH Minimally Invasive Access, date: 2001.
European Patent Office, Invitation to Pay Additional Fees for International Application No. PCT/US2012/036119, titled "Low-Profile Surgical Universal Access Port", mailed Jul. 13, 2012.
European Patent Office, European Search Report for European Application No. 12187933, titled "Insufflating Optical Surgical Instrument", dated Nov. 20, 2012.
European Patent Office, European Search Report for European Application No. 12187929, titled "Insufflating Optical Surgical Instrument", dated Nov. 20, 2012.
European Patent Office, European Search Report for European Application No. 12186716.2, titled "Bladeless Optical Obturator", dated Mar. 7, 2013.
European Patent Office, European Search Report for European Application No. 12186717.0, titled "Bladeless Optical Obturator", dated Mar. 7, 2013.
European Patent Office, European Search Report for European Application No. 12186712.1, titled "Bladeless Optical Obturator", dated Mar. 7, 2013.
European Patent Office, European Search Report for European Application No. 12186720.4, titled "Bladeless Optical Obturator", dated Mar. 7, 2013.
International Searching Authority, International Search Report and Written Opinion for International Application No. PCT/US2013/023458 titled "Adaptable Obturator for Various Sized Trocars", mailed Mar. 19, 2013.
European Patent Office, European Search Report for European Application No. 12186722.0, titled "Bladeless Optical Obturator", dated Mar. 20, 2013.
European Patent Office, European Search Report for European Application No. 12186721.2, titled "Bladeless Optical Obturator", dated Mar. 22, 2013.
European Patent Office, European Search Report for European Application No. 12186723.8, titled "Bladeless Optical Obturator", dated Mar. 22, 2013.
European Patent Office, European Search Report for European Patent No. 15185511, dated Jan. 14, 2016.

\* cited by examiner

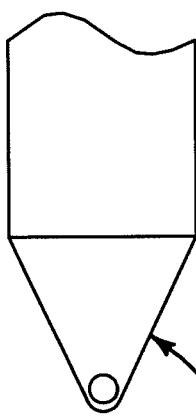
FIG. 10  19
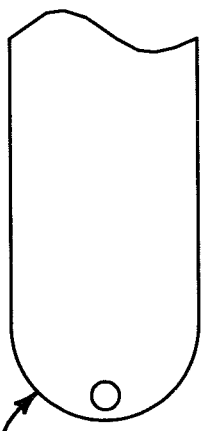
20  FIG. 11

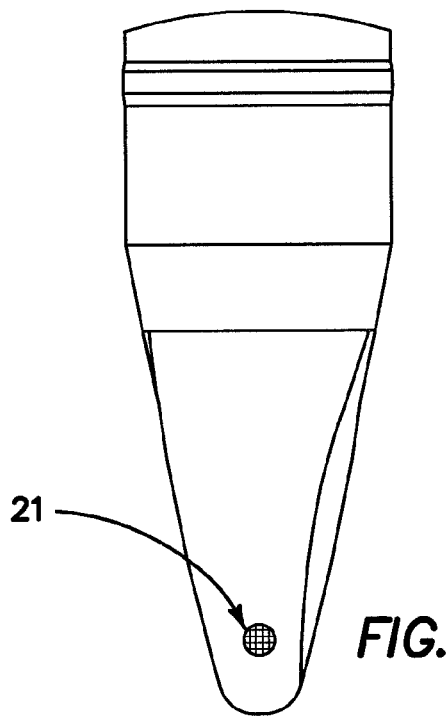
FIG. 12
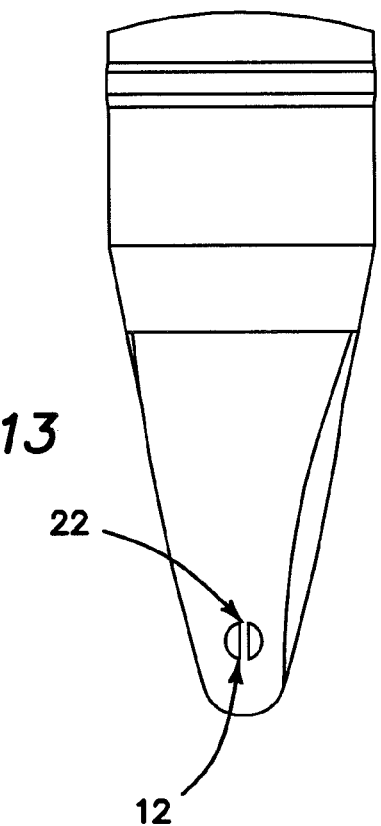
FIG. 13
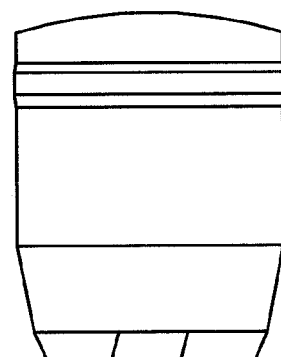
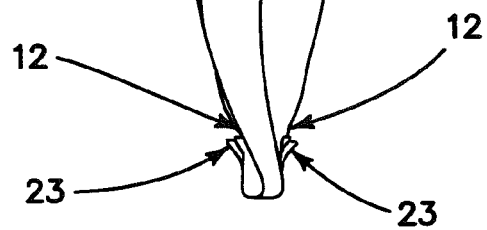
FIG. 14

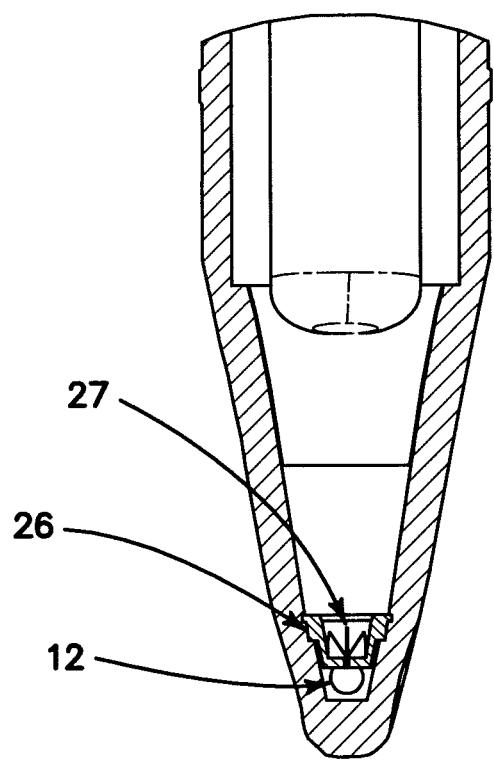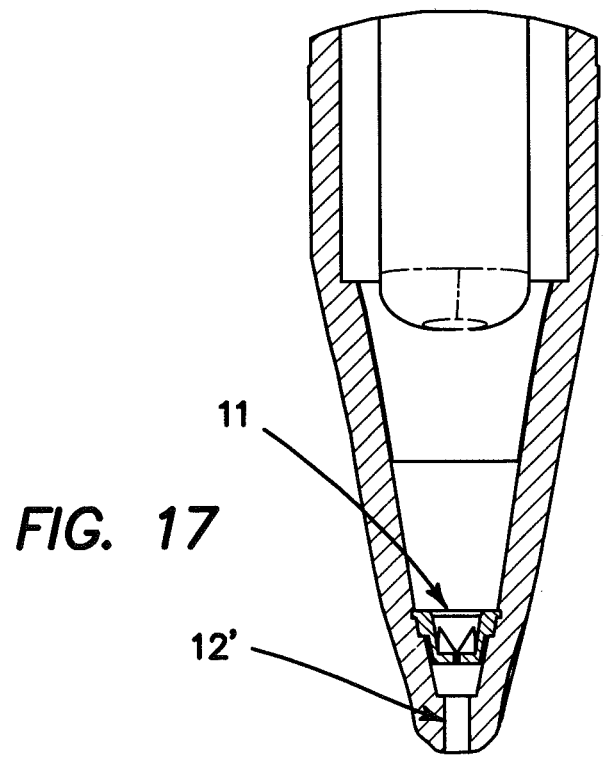

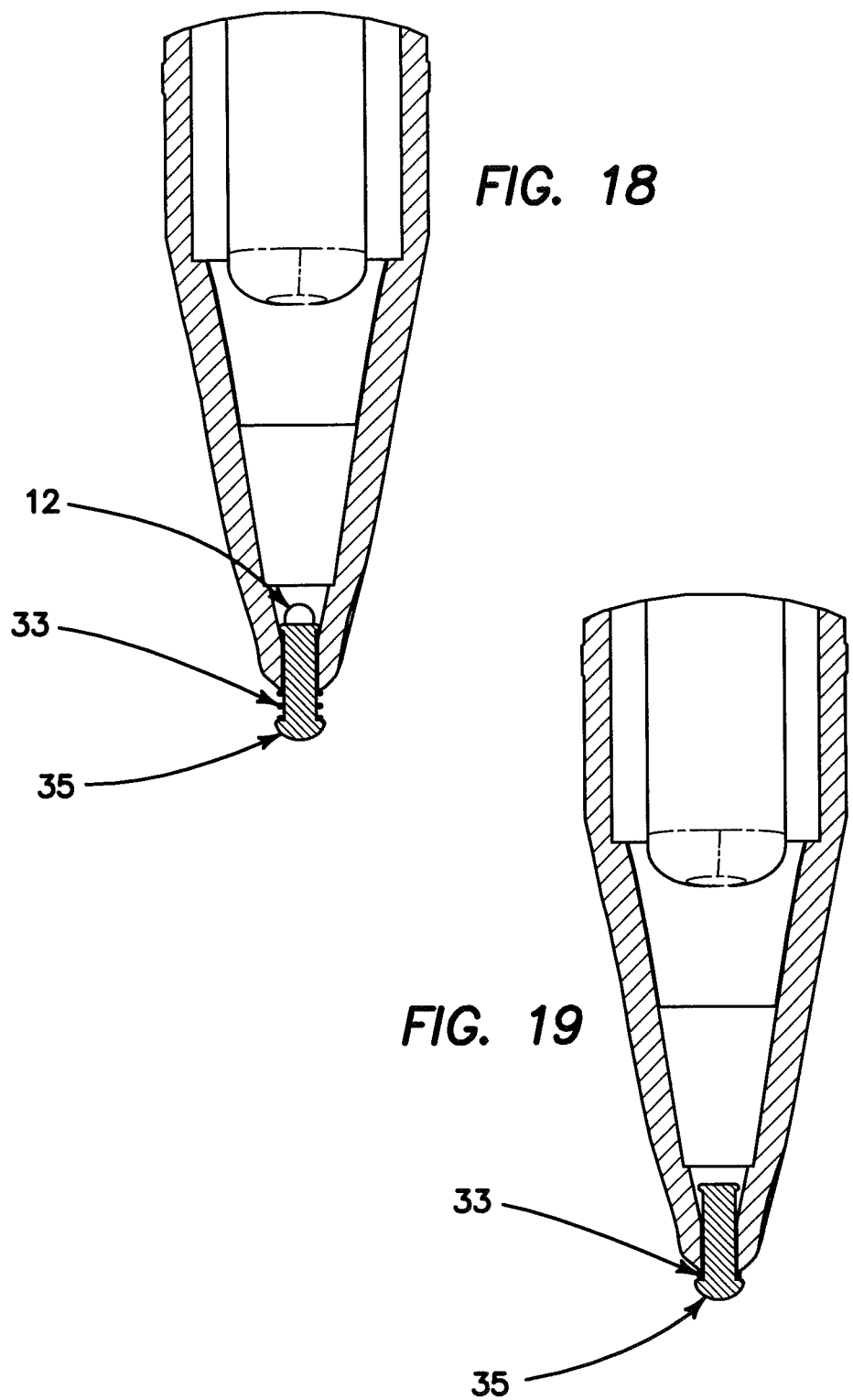

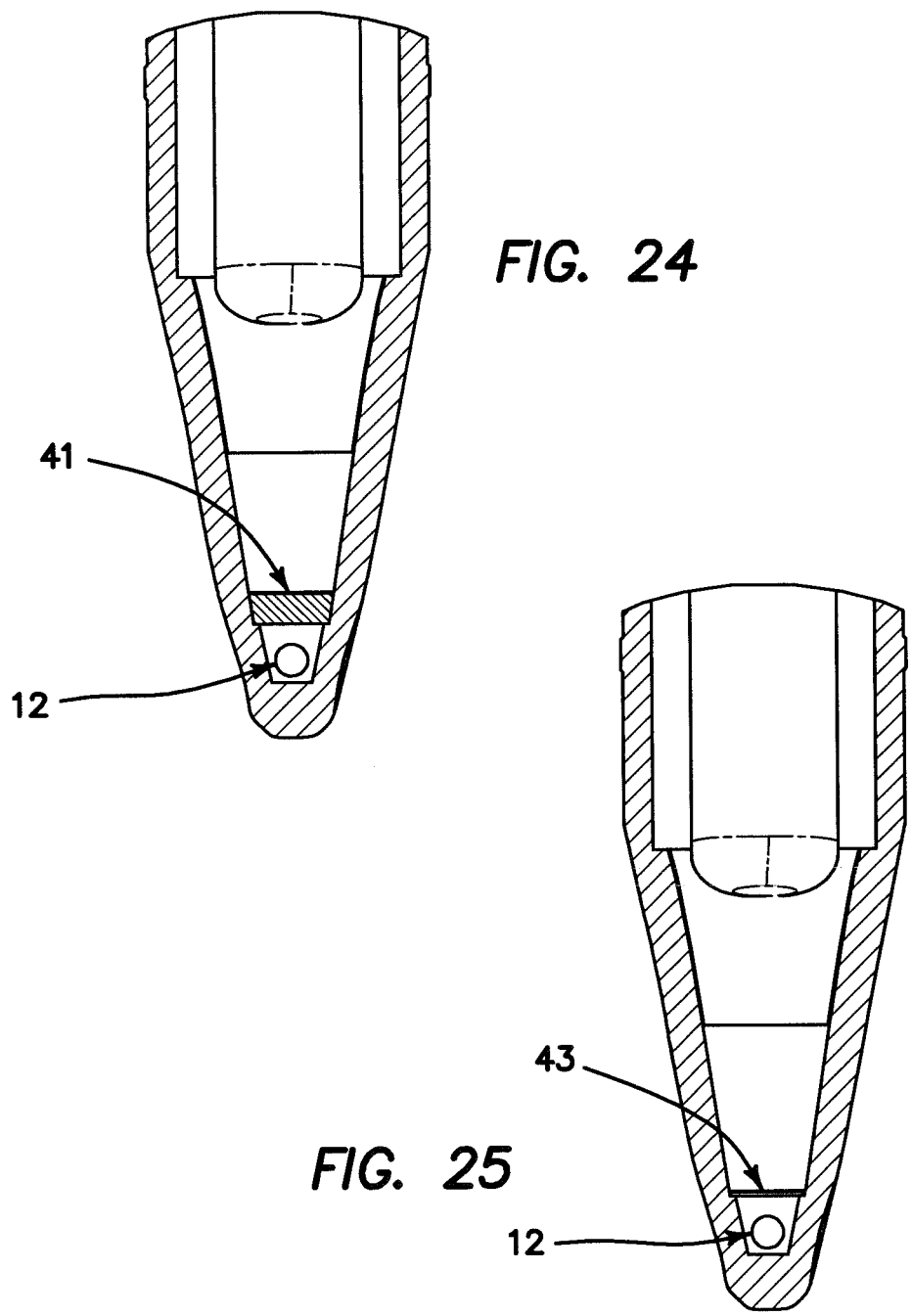

VISUAL INSUFFLATION PORT

CROSS-REFERENCE TO RELATED APPLICATIONS

This application is a continuation of co-pending U.S. patent application Ser. No. 11/868,883 filed on Oct. 8, 2007 entitled "Visual insufflation port" now U.S. Pat. No. 8,517, 977 issued on Aug. 27, 2013 which claims priority to and benefit of U.S. Provisional Patent Application No. 60/828, 529 filed Oct. 6, 2006 entitled "Visual insufflation port" the disclosures of which are hereby incorporated by reference in their entirety.

BACKGROUND

The present invention generally relates to surgical access devices for entering a patient's body, and in particular to visual insufflation obturators providing a visual and gaseous pathway.

Laparoscopic surgery of the abdominal area typically requires the introduction of an insufflation gas into the peritoneal cavity of the patient. The insufflation gas is usually pressurized to about 10 mm Hg above atmospheric pressure. This in turn lifts the abdominal wall away from the organs underlying it. Cannulas having seals are then placed at various locations through the abdominal wall to allow the use of a laparoscope and operating instruments. It is well known that establishing access to a non-inflated peritoneal cavity can be a very dangerous part of any laparoscopic procedure. The most common method to achieve insufflation is to pass a sharp needle through the abdominal wall and into the abdominal region, and then inject a gas through the needle and into the region thereby creating an enlarged or ballooned cavity to accommodate a laparoscopic procedure. Unfortunately, insertion of the needle has been required without any visual aid to facilitate location of the sharp needlepoint.

In order to reduce the probability of inadvertent penetration of delicate internal organs in this "blind" procedure, the sharp insufflation needle has been provided with a blunt or rounded member disposed within the lumen of the needle, and biased by a spring to an extended position beyond the needle tip. A drawback of this "blind" insertion is the surgeon may inadvertently contact the organs and tissues underlying the abdominal wall such as major blood vessels and the intestinal tract. Once access is gained, it can take several minutes for the gas to insufflate the abdomen and while this is happening the surgeon may be unaware of any complications caused by the insertion of the needle.

The Hasson technique can also be used to gain initial access to the peritoneal cavity. This technique involves making a mini-laparotomy and using the fingers to bluntly dissect the tissues of the abdominal wall and thereby creating an access similar to an open surgical procedure. Although generally considered less complicated, it can result in an access site that is not well suited for the subsequent introduction and use of a laparoscopic cannula. The cannula is typically held in place with an additional device that allows the cannula to be tied down with sutures to prevent it from slipping out of the abdominal wall. This may also leave a large defect and is difficult to perform in large abdominal walls.

Some surgeons have used trocar cannulas with an obturator for the initial entry into the peritoneal cavity. However, in order to allow the subsequent introduction of insufflation gas through the cannula, the trocar cannula must be inserted all the way through the wall of the abdomen and this in turn can be potentially dangerous as the tip of the trocar may have to advance as much as one inch beyond the distal surface of the abdominal wall and into the underlying anatomical structures. Additionally, the obturator must thereafter be removed in order to allow the introduction of the insufflation gas. As such, there remains a need in the art for an improved surgical instrument that provides enhanced visual entry and visual insufflation that minimizes the risks to organs, tissues and vessels underlying a body wall.

SUMMARY

A visual insufflation obturator/port is provided. In one aspect, a visual insufflation obturator comprises an elongate body having a proximal end, a distal end and a body lumen extending from the proximal end of the elongate body to the distal end of the elongate body. A handle is connected to the proximal end of the elongate body and has a handle lumen extending from a proximal end of the handle to the proximal end of the elongate body and is connected to the body lumen. A transparent tip is connected to the distal end of the elongate body and has a tip cavity. The tip has an outer surface with an aperture extending through the outer surface into the tip cavity and defines an insufflation gas pathway from the elongate body out through the aperture. A micro-seal is located within the tip cavity and is adjacent to the aperture.

In one aspect, a visual insufflation obturator comprises an elongate body having a proximal end, a distal end and a body lumen extending from the proximal end of the elongate body to the distal end of the elongate body along a longitudinal axis of the elongate body. A handle is connected to the proximal end of the elongate body. A transparent bladeless tip without cutting edges is connected to the distal end of the elongate body. The tip has a tip cavity and an outer surface with an aperture extending through the outer surface into the tip cavity and a micro-seal is located within the aperture of the tip between the outer surface and the tip cavity.

A visual insufflation obturator in one aspect comprises an elongate body having a proximal end, a distal end and a body lumen extending from the proximal end of the elongate body to the distal end of the elongate body. A handle is connected to the proximal end of the elongate body and has a handle lumen extending from a proximal end of the handle to the proximal end of the elongate body and is aligned to the body lumen. A transparent tip is connected to the distal end of the elongate body and has a tip cavity aligned to the handle lumen. The tip has a distal enclosed end and an outer surface extending from the distal end of the elongate body to the distal enclosed end with an aperture extending through the outer surface into the tip cavity. A laparoscope seal attached to the proximal end of the elongate body comprises an anti-fog applicator saturated with an anti-fog solution and positioned in a direct pathway through the seal and into the elongate body, the laparoscope seal having a zero seal and an instrument seal axially aligned to and preceding the zero seal.

In one aspect, a visual insufflation obturator comprises an elongate body having a proximal end, a distal end and a body lumen extending from the proximal end of the elongate body to the distal end of the elongate body. A handle is connected to the proximal end of the elongate body and has a handle lumen extending from a proximal end of the handle to the proximal end of the elongate body axially aligned to the body lumen. A transparent tip is connected to the distal end of the elongate body and has a tip cavity. The tip has an outer surface with an aperture extending through the outer surface into the tip cavity and a lens is located within the tip cavity before the aperture and a distal enclosed end of the transparent tip, the lens being coated with an anti-fog solution.

In one aspect, a visual insufflation obturator comprises an elongate body having a proximal end, a distal end and a body lumen extending from the proximal end of the elongate body to the distal end of the elongate body. At least one insufflation channel extends parallel to the body lumen starting from a body aperture positioned perpendicular to a longitudinal axis of the elongate body and through the elongate body to the body lumen defining an inflow insufflation gas pathway from outside the elongate body into the body lumen. A handle is connected to the proximal end of the elongate body and having a handle lumen extending from a proximal end of the handle to the proximal end of the elongate body axially aligned to the body lumen. A transparent bladeless non-cutting tip is connected to the distal end of the elongate body and has a tip cavity axially aligned to the handle lumen, the tip having a distal enclosed end and an outer surface extending from the distal end of the elongate body to the distal enclosed end with a tip aperture extending through the outer surface into the tip cavity and defining an outflow insufflation gas pathway from the at least one insufflation channel out through the tip aperture. Means for allowing antegrade insufflation gas flow out of the aperture and preventing retrograde insufflation gas flow into the elongate body, e.g., a micro-seal, is located within the tip cavity.

Many of the attendant features of the present invention will be more readily appreciated as the same becomes better understood by reference to the foregoing and following description and considered in connection with the accompanying drawings in which like reference symbols designate like parts throughout.

BRIEF DESCRIPTION OF THE DRAWINGS

FIGS. 7-14 are side views of various tips of an obturator in accordance with various aspects of the present invention;

FIGS. 15-27 are cross-sectional views of various tips of an obturator in accordance with various aspects of the present invention;

DETAILED DESCRIPTION OF THE INVENTION

Figure 1:
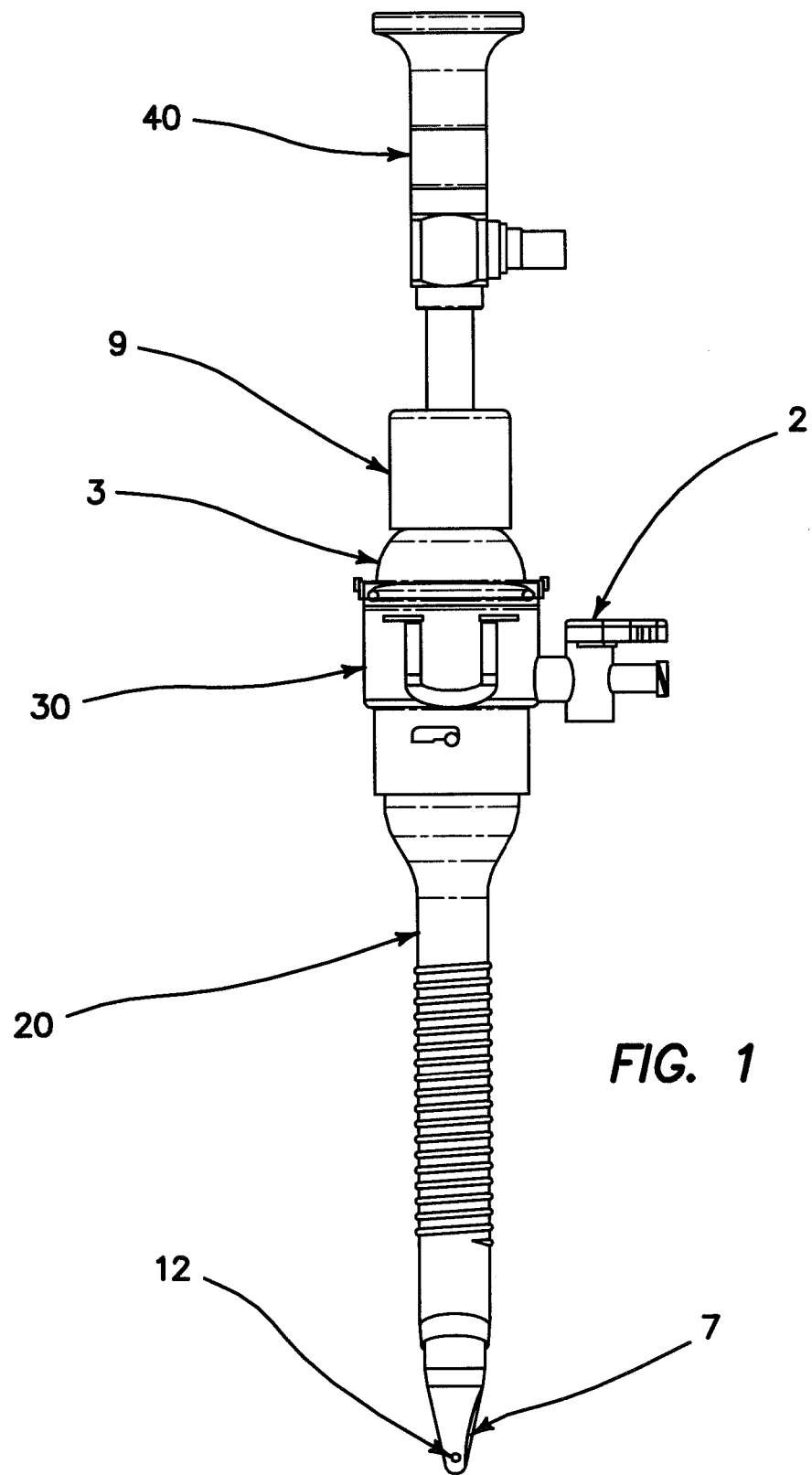
FIG. 1 is a side view of a visual insufflation port in accordance with various aspects of the present invention.
Figure 2:
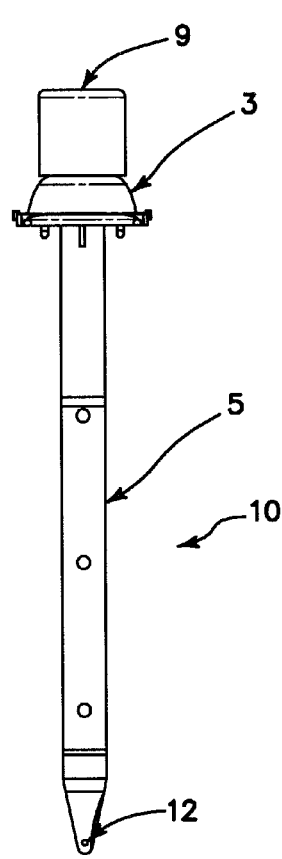
FIGS. 2-3 are side views of an obturator in accordance with various aspects of the present invention.
Figure 3:
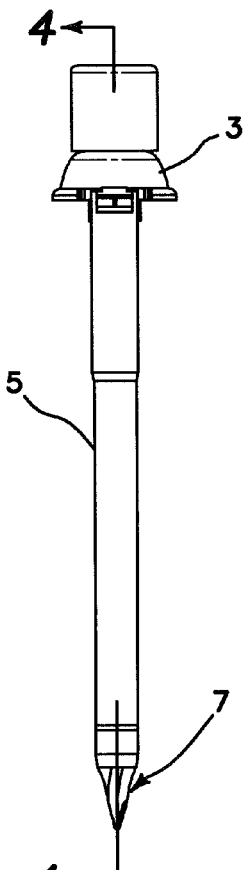
Figure 4:
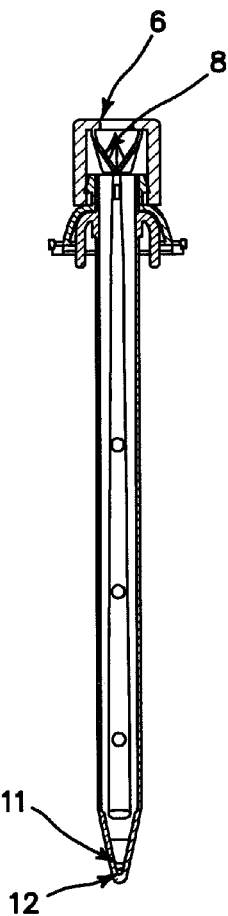
FIG. 4 is a cross-sectional view of an obturator in accordance with various aspects of the present invention.
Figure 5:
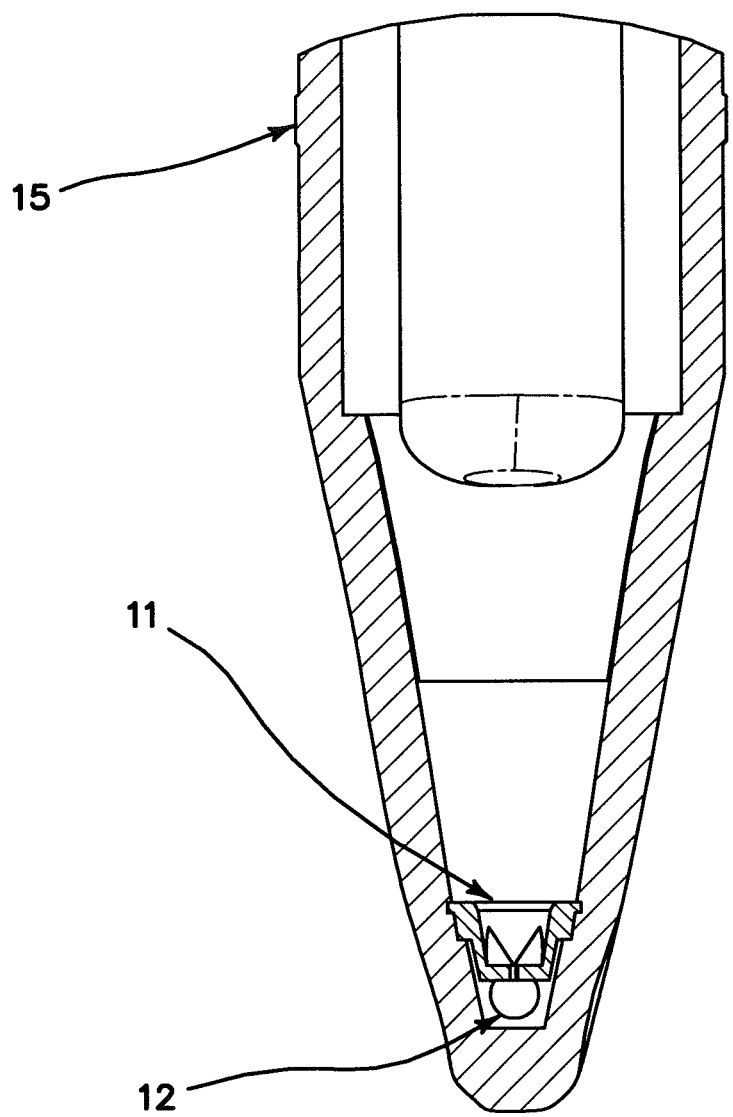
FIG. 5 is a cross-sectional view of a tip of an obturator in accordance with various aspects of the present invention.
Figure 6:
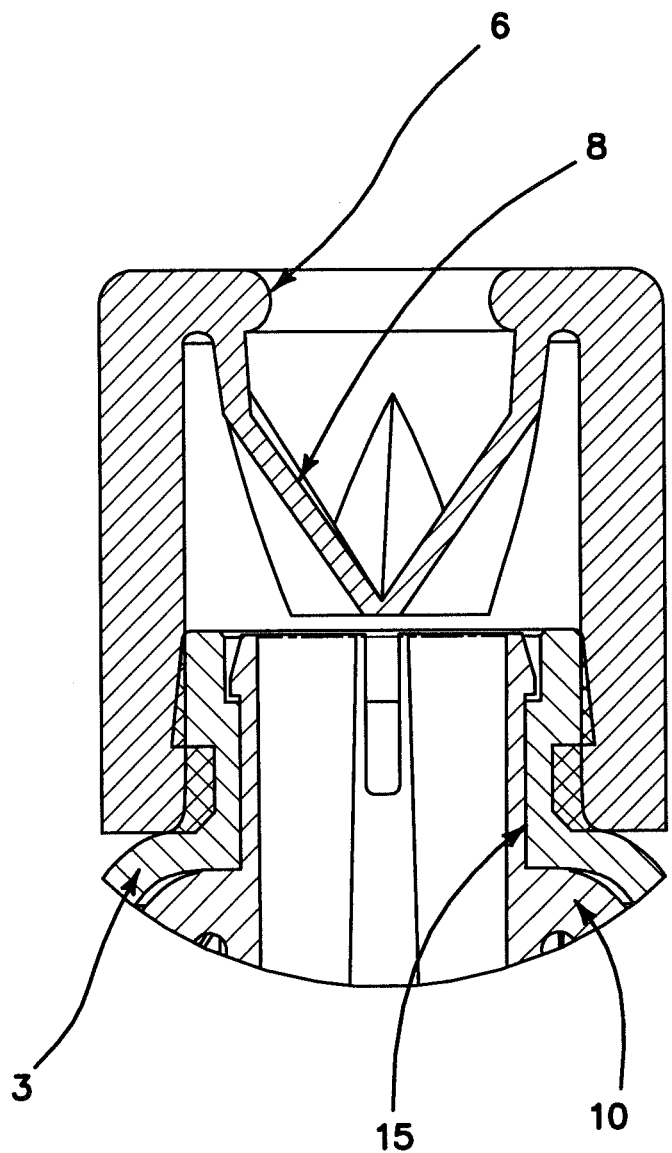
FIG. 6 is a cross-sectional view of a laparoscopic seal and a proximal end of an obturator in accordance with various aspects of the present invention.
Figure 7:
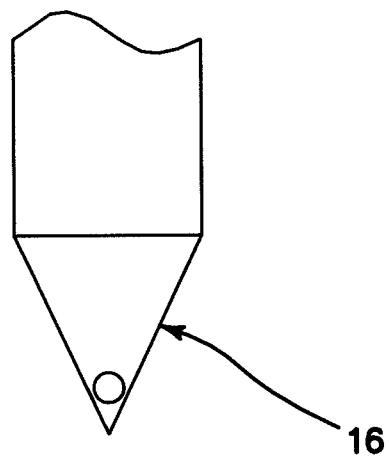
Figure 8:
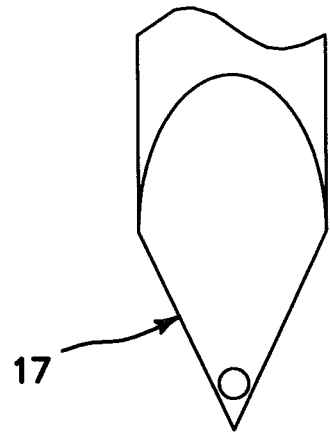
Figure 9:
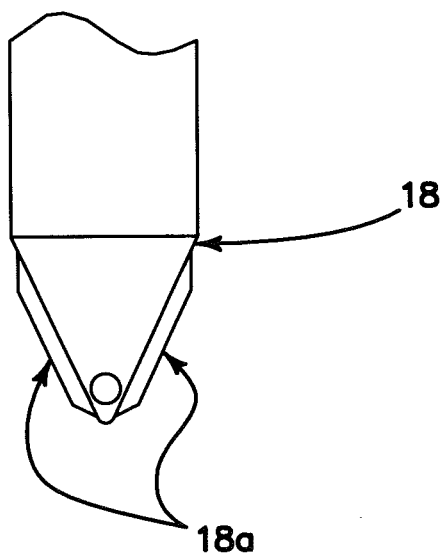

Aspects of an obturator with visualization and insufflation properties are provided. In one aspect, a micro-seal within the distal tip of the obturator enables the outflow (antegrade) of insufflating gasses such as carbon dioxide yet prevents the inflow (retrograde) of moisture and/or body fluids which could obstruct or impair the visualization properties through the distal tip of the obturator. The distal end of the obturator or portions thereof is formed of a material to enable visualization of tissue during the insertion of the obturator through a body wall. The obturator enables the insertion of a laparoscope 40, which typically includes an imaging element and fiber optic light fibers.

During an operational exemplary use, the obturator is inserted into and through trocar seal housing 30 and cannula 20. A laparoscope 40 is inserted into the proximal end of the obturator and advanced to the distal tip of the obturator. An endoscopic video camera is attached to the proximal end of the laparoscope. As the surgeon advances the trocar through the body wall, the surgeon can visually observe the tissue through the obturator tip as the tissue is being separated without cutting via a video monitor, which is connected to the endoscopic video camera. The surgeon can also readily determine when the body wall has been traversed to enable the most distal portion of the obturator to enter the body cavity. The most distal portion of the obturator includes insufflation vent holes or apertures through which an insufflation gas may flow from the obturator and into the peritoneal cavity. Insufflation of the abdominal cavity can then occur with minimal entry into the cavity by the obturator thereby reducing unintended contact with tissue or organs. The insufflated abdominal cavity enlarges the surgical area further reducing unintended contact and complications. The obturator can then be removed from the trocar cannula leaving behind a readily usable access port into the abdominal cavity.

A micro-seal is positioned just proximal to the insufflation apertures or vent holes on the obturator. The micro-seal is located inside the distal tip of the obturator and prevents the ingress of moisture and body fluids, which could impair or obstruct the visibility through the tip of the obturator. The micro-seal acting as a zero seal allows the flow of insufflation gas through the obturator and out through the insufflation vent holes.

In one aspect, the bladeless (non-cutting) obturator provides visualization of body tissue fibers as they are being separated, a controlled traversal across a body wall, and a trocar, which enables insufflation of a body cavity through the distal tip of the obturator. The obturator accommodates a laparoscope without imposing special requirement on the laparoscope used with the obturator. The bladeless obturator tip also extends beyond the distal end of the trocar cannula and thereby advances ahead of the trocar cannula that can have tips that are angled or shaped with a point or sharp tip. Thus, advancement of the trocar cannula and obturator can be accomplished while avoiding unintended contact by the trocar cannula.

As shown in FIGS. 1-6, a visual insufflation obturator is shown having an elongate body 5 extending from an obturator handle 3 to a distal tip 7. A laparoscope seal 9 is attached to the obturator handle 3. The elongate body or shaft 5 is hollow having a body lumen extending from the proximal end of the body to a distal end and continuing into a cavity formed in the tip 7. The tip is bladeless with non-cutting edges or surfaces. The handle 3 is hollow having a handle lumen extending from its proximal end to its distal end in communication with the body lumen of the elongate body 7. As such, a viewing channel or pathway is provided from the proximal end of the obturator handle 3 through the elongate body 5 to the tip 7. Also, a gaseous channel or pathway is provided from the elongate body 5 to the tip 7.

The tip 7 has one or more apertures or holes disposed through the tip. The aperture provides a gaseous pathway from the lumen (interior) of the elongate body and out through the aperture in the tip 7 (exterior of the obturator). In one aspect, one or more apertures or holes through the elongate body provides a gaseous pathway for the flow of insufflation gas from a trocar cannula into the elongate body and out through the aperture in the tip 7, the tip extending beyond the distal end of the trocar cannula. The elongate body, in one aspect, can have one or more insufflation channels embedded in or attached to the walls of the elongate body in gaseous communication with the aperture(s) in the tip. Pressurized insufflation gas in one aspect is introduced through the stopcock 2 into the trocar cannula 20. Trocar seal housing 30 prevents the gas from escaping proximally out from the cannula 20. The gas from the trocar cannula 20 enters the one or more apertures or holes in the elongate body and flows out distally through the aperture in the tip.

The tip 7, in one aspect, has a micro-seal 11 positioned therein through which insufflation gasses may flow and then out through the hole or aperture 12 in the tip. However, the micro-seal acting as a zero seal is normally closed and therefore prevents moisture and body fluids from flowing into the tip of obturator. In the absence of the micro-seal, moisture and body fluids could flow into the tip 7 of the obturator and create condensation on the inner walls or lumen of the obturator (e.g., elongate body and/or tip) and on the lens of the laparoscope. The condensation can diminish the visibility through the obturator and in some cases, can entirely obstruct the view through the tip 7 of the obturator. The micro-seal 11 prevents the ingress of moisture and body fluids and therefore enhances the visibility through the tip of the obturator while also enabling the flow of insufflation gasses through the tip of the obturator. The micro-seal size is substantially diminished in size and thereby reduces obstruction of the view of a laparoscope inserted into the obturator. In one aspect, the micro-seal is about 2 to 4 mm in diameter and about 2 to 3 mm tall. The micro-seal provides a one-way pathway allowing insufflation gas to flow out through the tip while preventing gas, fluid, etc. from entering back through the micro-seal.

The obturator handle 3 provides a place for a surgeon to hold or grasp the obturator. The obturator handle 3 as shown has a generally domed shape that is connectable to a trocar seal housing 30. In one aspect, the handle is a pistol-like grip or generally flanged portion providing finger grips. The obturator handle, in one aspect, can also be manipulated to apply torque to the obturator for insertion of the obturator into the body cavity.

In one aspect, a laparoscope seal 9 is positioned at the proximal end of the obturator handle 3. The laparoscope seal 9 has a zero seal 8 preventing the egress of insufflation gases when the obturator is used without an inserted laparoscope. The laparoscope seal 9 also includes a septum seal 10 forming a seal with a laparoscope to prevent the egress of insufflation gases when the obturator is used with an inserted laparoscope. The zero seal 8 in one aspect is a double duckbill valve that minimizes the forces utilized to insert and remove the laparoscope. By minimizing the forces to insert and remove the laparoscope from the laparoscope seal 9, the application of lubricants such as silicone grease or silicone fluid on the laparoscope seal is obviated or minimized. Some form of lubrication such as silicone grease or silicone fluid can be used to reduce the insertion and removal forces of laparoscopic instrumentation. These lubricants however can be transferred to the lens of a laparoscope as the laparoscope is inserted through the trocar seal resulting in distorted and diminished visibility through the laparoscope. As such, the laparoscope seal 9 in one aspect enables the laparoscope to be inserted into the obturator and withdrawn from the obturator with minimal force while ensuring that optimal visibility through the laparoscope is maintained.

The laparoscope seal 9 also minimizes the torque required to rotate the obturator relative to the inserted laparoscope. The trocar cannula with the optical obturator is rotated in an alternating clockwise and counterclockwise fashion during traversal across a body wall. During this time, it is desirable to keep the laparoscope in a rotationally fixed position relative to the trocar and the optical obturator to ensure a stable image on the video monitor. The double duckbill valve incorporated into the laparoscope seal enables the obturator to be easily rotated relative to the inserted laparoscope.

In one aspect, the micro-seal 11 that prevents the ingress of moisture is located entirely within the inner walls of the tip 7 of the obturator. With the micro-seal being an internal component, it is not possible to dislodge or separate the micro-seal from the obturator and thereby fall into the surgical site. The micro-seal 11 in one aspect is a double duckbill configuration, which enables the maximum flow rate through the valve while minimizing the overall size of the duckbill valve. The double duckbill valve also reduces the amount of pressure required to open the duckbill valve during initial flow of insufflation gasses. This can be desirable as some pressures used during the insufflation of a body cavity are low, e.g., about 15 mm Hg.

The duckbill or double duckbill valve 11 in one aspect is a single-piece component, which is injection molded of a transparent material such as silicone or Kraton® to ensure that visibility through the duckbill valve is achieved and thereby ensuring a further reduction in potential obstruction of a laparoscope's view. The duckbill valve 11 in one aspect is molded from an opaque material such as polyisoprene to provide contrast between the duckbill valve and the obturator. The duckbill valve 11 in one aspect is tinted or colored to provide contrast and to visually indicate proper positioning of the distal tip of the obturator relative to a body wall.

The duckbill valve 11 is fixed in position via an interference slip fit within the obturator. The obturator in one aspect has a small cylinder or cylindrical spacing formed or carved within the tip of the obturator that is in fluid communication with the insufflation vent holes. The duckbill valve 11 is inserted into the cylinder, e.g., via a mandrel and remains in place via the interference slip fit and thereby avoids the use of adhesives or other attachments that may obstruct a laparoscope's view. In one aspect, a flange, lip or projection portion of the micro-seal is wedged into the cylindrical space in which a ledge engaged with the flange secures the micro-seal in place.

The obturator in traversing the body wall or conduit can encounter fluids, such as gastric fluids that may damage a laparoscope, and tissue, e.g., fat that may obscure the laparoscope's view. The micro-seal prevents such fluids and tissue from contacting the laparoscope (often an expensive and delicate instrument). The introduction of insufflation gas via the insufflation gas pathway through the micro-seal and out of the tip aperture can also clear the view by expelling fluid or tissue that entered inside and/or positioned around the tip. The obturator also allows subsequent use of the obturator in the same surgical procedure, for example, use for a second, third or more insertion sites as used in some laparoscopic procedures. The micro-seal acting as a zero seal prevents the egress or escape of gas from the insufflated cavity or conduit. As such, the obturator could be used to form additional insertion sites into the insufflated cavity without losing pneumoperitoneum. The subsequent use of the obturator reduces surgical cost, time and other issues that arise from instrument exchanges or introducing additional instruments to the surgical procedure. The micro-seal can also obviate the use of other seals with the initial and/or subsequent use of the obturator.

In one aspect, the obturator shaft 5 is configured with integral sealing bands 15 at either distal or proximal ends or both to affect a seal between the obturator 10 and mating components of a trocar or other portions of the obturator to prevent the egress of insufflation gases. The obturator 10 in one aspect has a small integral band of material 15 at its distal tip designed to create an interference fit between the obturator 10 and the trocar cannula 20 with the obturator inserted into the trocar cannula. The interference fit prevents the outflow of insufflation gas between the outer wall of the obturator and the inner bore of the cannula 20. The obturator in one aspect has a small integral band of material 16 at its proximal end arranged to create an interference fit between the outer wall of the obturator 10 and the inner wall of the trocar handle/seal housing 30. The interference fit prevents the outflow of insufflation gas between the inner bore of the trocar handle 30 and the outer wall of the obturator 10.

In one aspect, the laparoscope seal 9 prevents the egress of insufflation gas and is positioned on the proximal end of the obturator handle 3 via a snap fit with the handle. The laparoscope seal comprises a proximal septum seal 6 and a distal double duckbill valve 8. The laparoscope seal in one aspect is a single-piece component, which is injection molded of a transparent or opaque elastomeric material such as silicone, polyisoprene, or Kraton. The laparoscope seal 9 in one aspect is coated with a dry lubricant or treated with various materials to further reduce the forces used to insert and withdraw a laparoscope 40 and/or reduce the friction associated with insertion and withdrawal of the laparoscope. Examples of such coatings and treatments include Teflon® coatings, parylene coatings, plasma surface treatments, and chlorination treatments. In one aspect, the duckbill valve of the laparoscope seal 9 is a single duckbill valve.

As shown in FIGS. 7-11, the tip 7 of the obturator can have varied configurations each providing a particular functionality and characteristics utilized in a particular surgical procedure and/or user. For example, the obturator has a sharp pointed tip 16 (FIG. 7), a pyramidal tip 17 (FIG. 8), a bladed tip 18 (FIG. 9), sharp edges 18a, or sharpened edges to facilitate traversal through body tissue. The obturator in one aspect has a conical blunt tip 19 configuration to facilitate traversal through body tissue (FIG. 10). The obturator has a radiused blunt tip 20 for traversal through an existing body orifice or through relatively soft or fatty tissue (FIG. 11). In one aspect, the tip is bladeless with no cutting or sharp edges or surfaces. The bladeless tip in one aspect has a generally tapered configuration with an outer surface extending distally to a blunt point with a pair of side sections having a common shape and being separated by at least one intermediate section. The side sections extend from the blunt point radially outwardly with progressive positions proximally along the axis. With this aspect, the tapered configuration facilitates separation or spreading of different layers of the body tissue and provides proper alignment of the tip between the layers. The distal portion of the side sections are twisted radially with respect to the proximal portion of the side sections. The distal portion of the intermediate section is twisted in a first radial direction and the proximal portion of the intermediate section is twisted in a second radial direction opposite the first radial direction. Each tip has an insufflation vent hole or aperture 12 and a micro-seal placed within the tip adjacent to the vent hole 12. The tip 7 and/or shaft 5 or portions thereof in one aspect can formed of a rigid material, flexible material or a combination thereof.

In one aspect, the tip provides and allows viewing through the tip or portion thereof, for example, by using a laparoscope inserted into the obturator. The tip or portions thereof is transparent. One would recognize that transparent would include translucent and other means that provides/allows viewing through at least a portion of the tip with a laparoscope. Windows, viewing channels or magnifiers could be also added or embedded into the tip to enhance laparoscope vision. The tip in one aspect may have one or more indicators, markings or deformations on the tip for example to identify the position of the tip. Such indicators may have to be positioned close to the aperture to prevent interference with the viewing path of the laparoscope. Likewise, the aperture and/or micro-seal are positioned close to the most distal portion of the tip to also prevent interference with the viewing path of the laparoscope. For example, the aperture may be a few millimeters from the distal portion of the tip and a micro-seal a few millimeters away from the aperture.

Referring now to FIGS. 12-13, the obturator, in one aspect, has screens 21 across the insufflation apertures or vent holes 12 to prevent the ingress of body tissue such as fat into the insufflation vent holes and into tip 7 of the obturator. In place or in addition to the screens, the insufflation vent holes are configured with raised ribs 22 across the diameter of the holes to deflect body tissue away from the holes and thereby prevent the ingress of body tissue into the vent holes and into the tip of the obturator. As shown in FIG. 14, the obturator could also include integral tissue deflectors 23 just distal to the insufflation vent holes that would serve to move body tissue away from the holes and thereby prevent the ingress of body tissue into the holes and into the tip of the obturator. In one aspect, the tissue deflectors 23 are attached to the tip 7 and are made of an elastomeric material, such as rubber.

In one aspect, the internal micro-seal 11 is coated or treated with various materials to enable the duckbill valve to be slightly opened with less force and to increase the insufflation fluid flow characteristics of the duckbill valve. Examples of such coatings and treatments are Teflon® coatings, parylene coatings, plasma surface treatments, and chlorination treatments.

Figure 15:
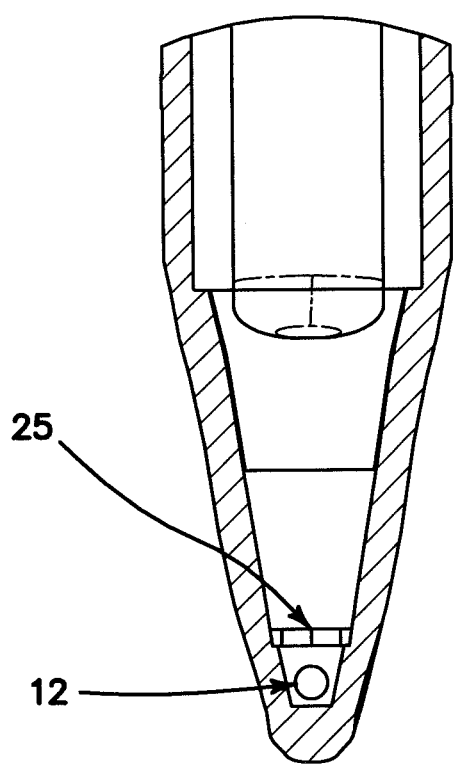

The internal micro-seal prevents the ingress of moisture and body fluids into the distal tip of the obturator. As previous described and also shown in FIGS. 15-16, the internal micro-seal of the obturator can have varied configurations each providing a particular functionality and characteristics utilized in a particular surgical procedure and/or user. For example, the internal micro-seal is a single or double duckbill valve, a flat disc type valve 25 with either a single slit or a plurality of slits, a double duckbill valve 26 with slits 27 running parallel to the distal end surface of the duckbill and to the longitudinal axis of the duckbill or a combination of valves thereof. In one aspect, the double duckbill valve with slits running parallel to the distal end surface of the duckbill and to the longitudinal axis of the duckbill are lengthen to run up the sides of the duckbill valve, thereby increasing the flow rate through the duckbill valve. In one aspect, the double duckbill valve has a single slit, which runs parallel to the distal end surface of the duckbill and to the longitudinal axis of the duckbill.

As previously described, the obturator is configured with the internal micro-seal and an insufflation vent hole at the most distal portion of the obturator tip next to the internal micro-seal. As shown in FIG. 17, the vent hole 12' in one aspect is generally coaxial with the longitudinal axis of the obturator. The micro-seal 11 would normally be closed to prevent the ingress of moisture and body fluids. Under pressure from the insufflation gas, the micro-seal 11 would open to enable the flow of the insufflation gas into the body cavity.

Various other exemplary micro-seals will now be described. In FIG. 19, the obturator includes an external spring biased tip 35 at its distal end adjacent to the vent hole 12. The spring 33 biases the tip in a distal position. During traversal across a body wall, the body wall provides a compressive force on the spring tip 35 moving it to a proximal or sealed position. While in the proximal position, the spring tip 35 prevents the ingress of moisture and body fluids into the obturator by sealing the insufflation vent hole 12. Once the tip of the obturator enters the body cavity, the spring tip 35 deploys into the distal unsealed position. The insufflation gas is then transferred through perpendicular vent holes 12 and into the body cavity. The spring tip 35 in one aspect through movement between the sealed and unsealed positions and vice versa or color coding the tip, the spring tip 35 provides a visual indication to the surgeon that access into the body cavity had been achieved. The spring tip 35 in one aspect can provide an audible indication, e.g., a snap, to the surgeon that access into the body cavity had been achieved.

Figure 20:
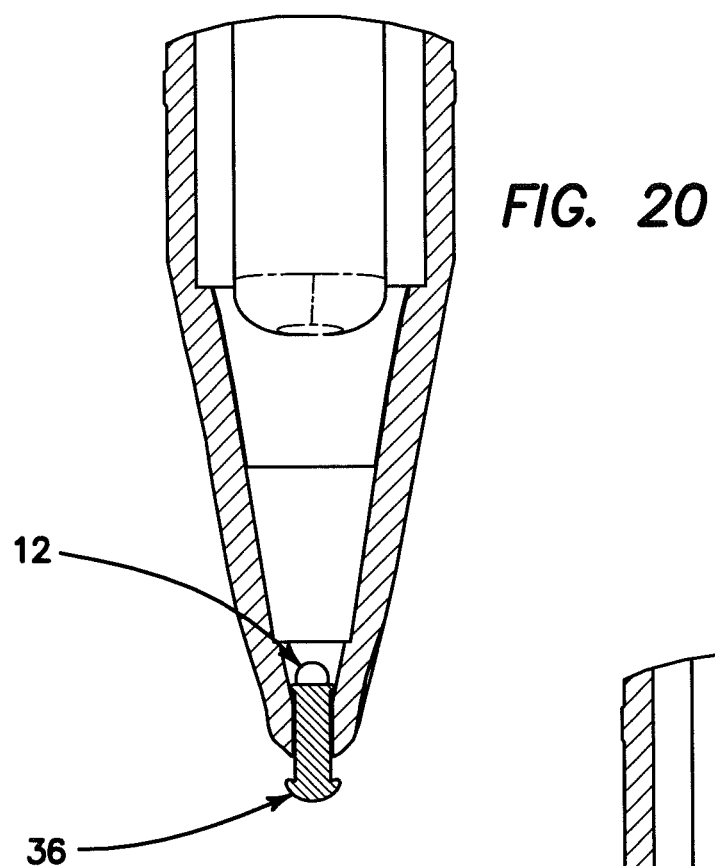
Figure 21:
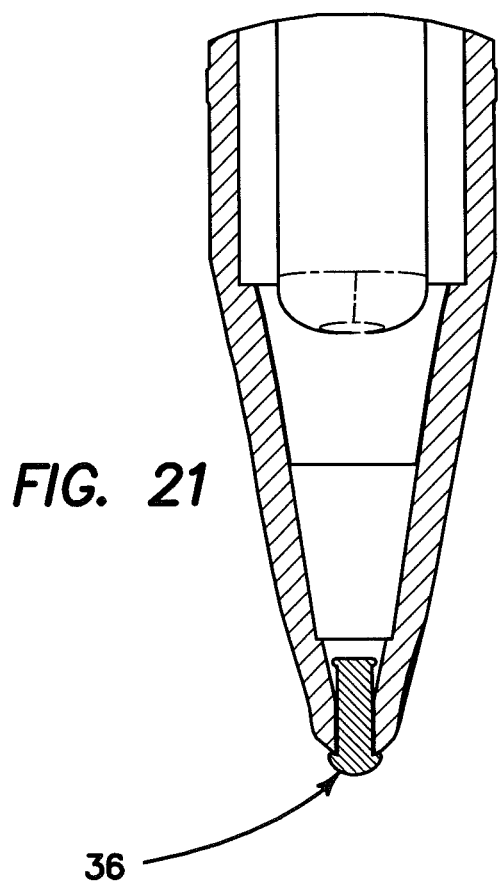

Referring now to FIGS. 20-21, in one aspect, the obturator has a non-biased moveable tip 36 at its distal end. The tip 36 is initially positioned in a distal unsealed position. During traversal across a body wall, the body wall provides a compressive force on the tip moving it to a proximal sealed position covering and sealing the vent hole 12. While in the proximal position, the tip 36 prevents the ingress of moisture and body fluids into the obturator. Once the tip of the obturator enters the body cavity, the movable tip would remain in the proximal sealed position. During pressurization of the obturator via insufflation gas, the moveable tip 36 would be forced to the distal unsealed position thus allowing the flow of insufflation gas through the vent hole 12 and into the body cavity. The movable tip in one aspect also comprises an o-ring or an elastomeric seal at its proximal end to assist in sealing the movable tip 36 with the internal walls of the obturator.

Figure 22:
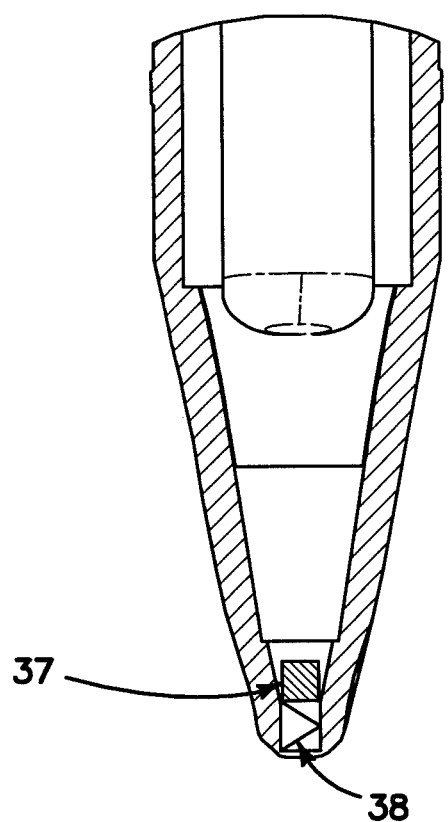
Figure 23:
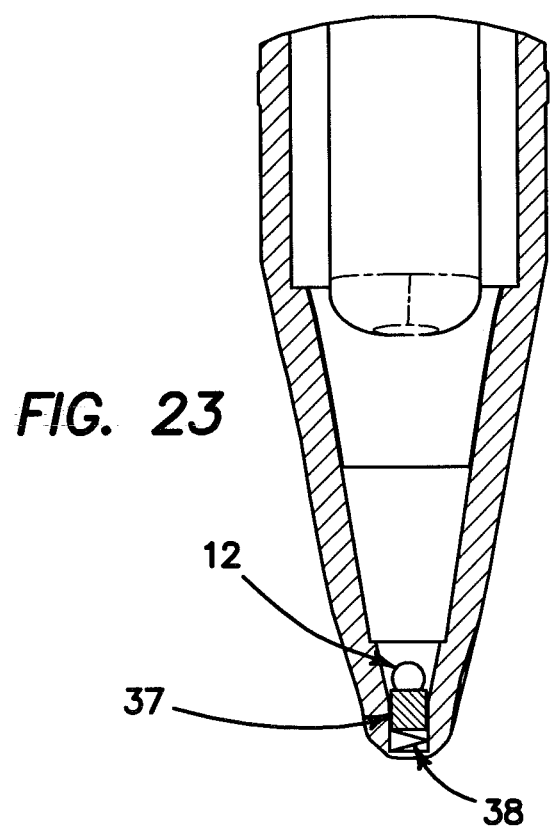

In FIGS. 22-23, the obturator in one aspect has an internal check valve in the distal tip of the obturator near the vent hole 12. The check valve comprises a piston 37 in a cylinder with a spring 38 positioned below the piston such that the piston is biased in a proximal sealed positioned. In the proximal sealed position, the piston seals one or more perpendicular insufflation vent holes 12. During pressurization of the obturator via insufflation gas, the top of the piston is exposed to the pressure and thus is moved to a distal unsealed position allowing the insufflation gas to flow through the vent holes 12 and into the body cavity. The piston 37 in one aspect is injection molded of a transparent polycarbonate material.

In FIG. 24, the obturator in one aspect has a membrane 41 positioned inside the distal tip 7 of the obturator which prevents the ingress of moisture and body fluids from the vent hole 12 yet allows insufflation gasses to flow through the membrane 41 and out the vent hole 12. The membrane 41 is porous and is formed from a hydrophobic material such as Gore-Tex® material. The membrane 41 is inserted into a small cylinder within the distal tip of the obturator adjacent to the insufflation vent hole 12. The membrane in one aspect is also bonded or welded to the inside wall of the distal tip 7 of the obturator.

Referring now to FIG. 25, in one aspect, the obturator has a perforated membrane 43 positioned inside the distal tip 7 of the obturator, as an alternative to a duckbill valve, for example, which prevents the ingress of moisture and body fluids from the vent hole 12. The perforated membrane 43 tears open or bursts apart when exposed to the pressure of the insufflation gas allowing the insufflation gas to flow out through the insufflation vent holes 12 and into the body cavity. The membrane 43 is formed from paper, cellophane, polyethylene, or polyurethane. The membrane 43 provides a single use visual insufflation port. For example, once the membrane 43 tears open and the insufflation gas flow halts, the ingress of moisture and/or body fluids will not be stopped by the torn perforated membrane 43. Thus, the re-use of the obturator is prevented thereby if so arranged the obturator can be designated as a disposable or single-use instrument preventing unintended operation or improper sterilization of the used obturator.

Figure 26:
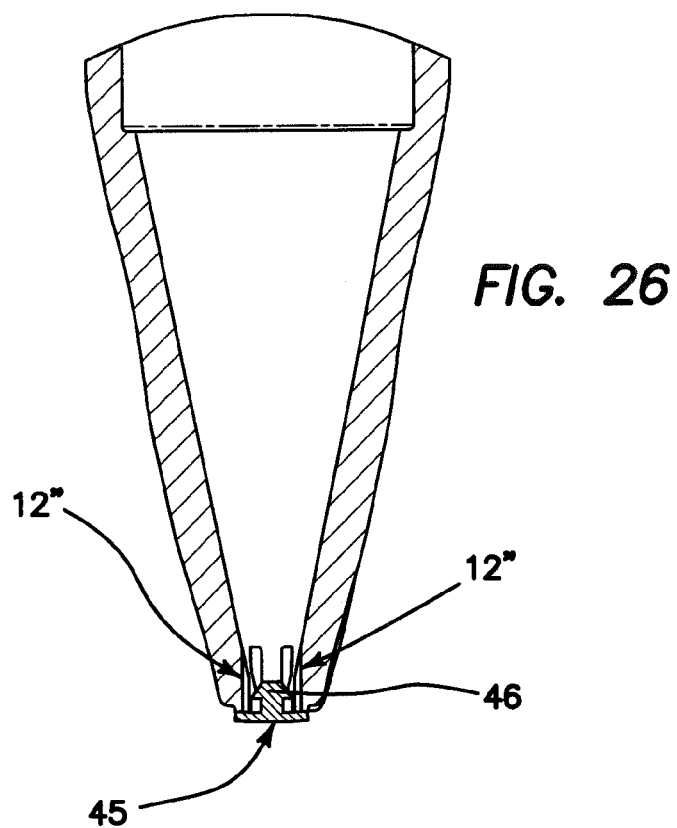

As shown in FIG. 26, the obturator in one aspect has an elastomeric external valve 45 such as an umbrella valve at the distal end of the obturator. The umbrella valve 45 is flush with the distal end of the obturator and covers longitudinal insufflation vent holes 12". The umbrella valve moves distally relative to the tip 7 of the obturator when exposed to the pressure of the insufflation gas. The insufflation gas flows though the vent holes into the body cavity. The umbrella valve 45 is attached to the distal tip of the obturator via an integral elastomeric stem 46, which runs through a central axial hole in the obturator. As the obturator is pressurized via the insufflation gas, the elastomeric stem 46 elongates to enable the external portion of the umbrella valve 45 to move distally thus unblocking the vent holes 12" and allowing insufflation gas to flow through the vent holes and into the body cavity. The umbrella valve 45 in its initial or normal condition also prevents the ingress of moisture and body fluids into the obturator during insertion into a body cavity by blocking the vent holes 12" and ensures that optimal visibility through the laparoscope and the obturator is maintained. The umbrella valve 45 in one aspect is a single-piece component, which is injection molded of a transparent or opaque silicone, polyisoprene, or Kraton® material.

Figure 27:
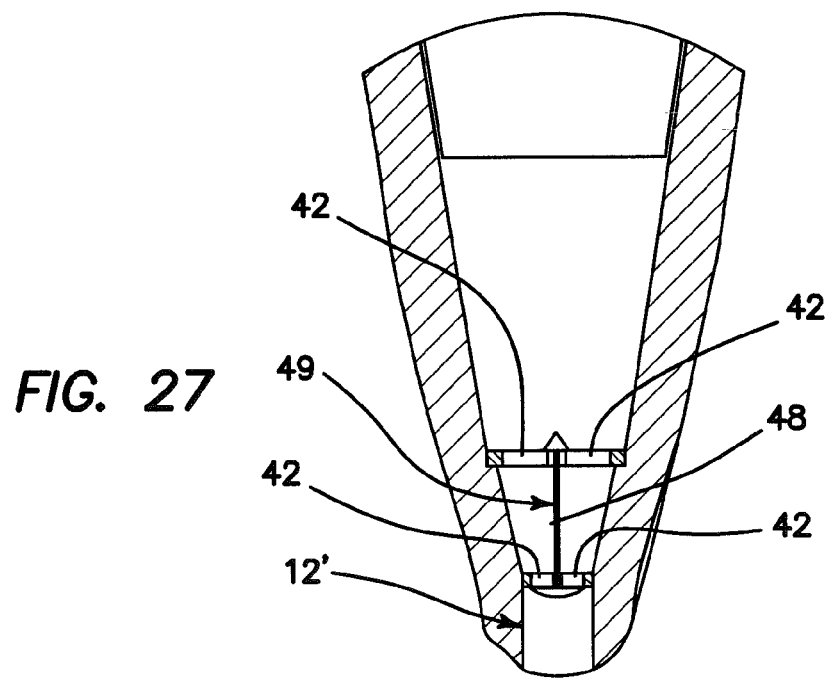

In FIG. 27, in one aspect, the obturator has an elastomeric internal umbrella valve 49 at the distal end of the obturator. The umbrella valve 49 is positioned just proximal to perpendicular or longitudinal vent hole 12' at the distal tip of the obturator. The umbrella valve 49 covers one or more intermediate flow channels 42 to prevent the ingress of moisture and body fluids into the obturator during insertion into a body cavity. During pressurization from the insufflation gas, the elastomeric stem 48 of the umbrella valve 49 elongates to enable distal movement of the umbrella valve thus allowing the insufflation gas to flow through the intermediate flow channel or channels 42, out through the insufflation vent hole 12', and into the body cavity. The internal umbrella valve 49 in one aspect is a single-piece injection molded component formed from a transparent or opaque silicone, polyisoprene, or Kraton® material.

Figure 28:
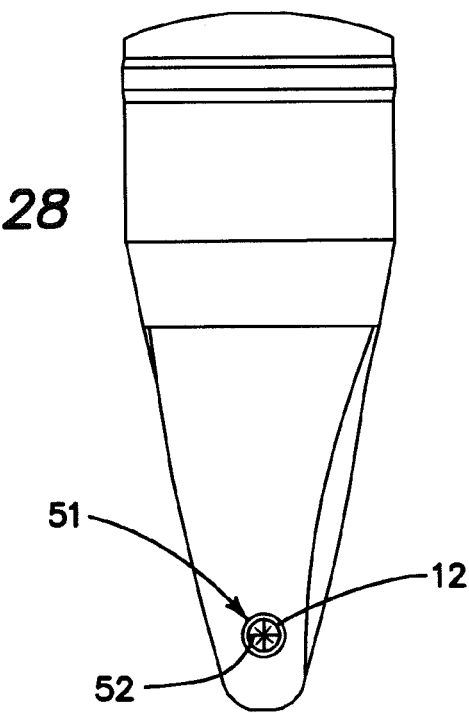
FIG. 28 is a side view of a tip of an obturator in accordance with various aspects of the present invention.

In FIG. 28, the obturator in one aspect comprises one or more over-molded elastomeric valves 51 at the tip 17 of the obturator. The elastomeric valves 51 in one aspect are flat disc type valves that are formed of materials such as polyisoprene, Kraton®, and silicone materials. The elastomeric valves 51 encases perpendicular insufflation vent holes 12 at the distal tip 7 of the obturator and with slits 52 in the valves, such that the slits are normally closed to prevent the ingress of body fluids and moisture. Under pressure from the insufflation gas, the slits 52 in the valves slightly open enabling the insufflation gas to flow into the body cavity. Once pressure from the insufflation gas is removed, the slits 52 in the valves close thereby preventing the ingress of body fluids and moisture through the vent holes 12.

Figure 29:
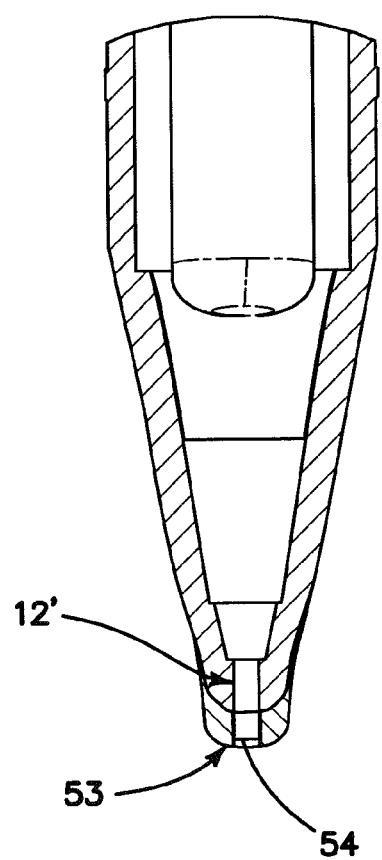
FIGS. 29-33 are cross-sectional views of various tips of an obturator in accordance with various aspects of the present invention.

As shown in FIG. 29, in one aspect the obturator has a single over-molded elastomeric valve 53 covering a portion or apex portion of the distal tip 7. The elastomeric valve 53 encases a single longitudinal insufflation vent hole 12' at the distal tip 7 of the obturator. The elastomeric valve 53 has a slit 54 at its distal end or apex generally aligned with the longitudinal vent hole 12' such that the slit 54 is normally closed to prevent the ingress of body fluids and moisture. Under pressure from the insufflation gas, the slit 54 in the valve slightly opens enabling the insufflation gas to flow into the body cavity. The elastomeric valve 53 in one aspect also encases a pair of perpendicular insufflation vent holes. The elastomeric valve in one aspect encases a plurality of longitudinal insufflation vent holes 12' at the distal end of the tip 7 of the obturator.

Figure 30:
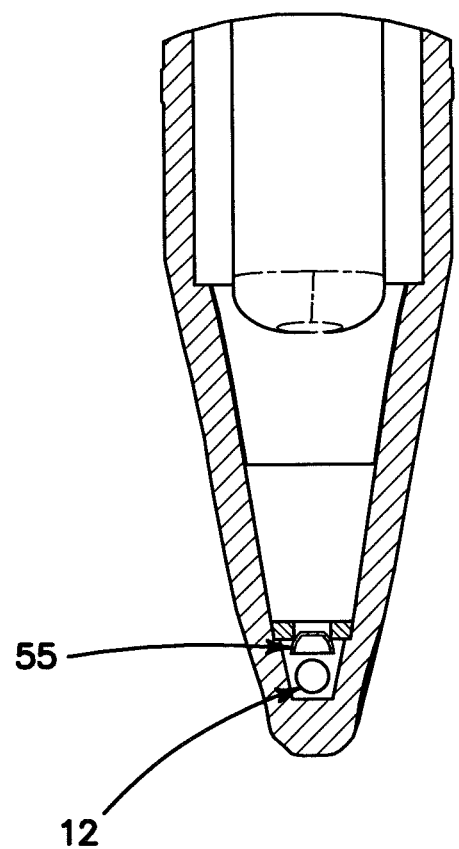

Referring now to FIG. 30, in one aspect, the obturator has an internal elastomeric flapper valve 55 located proximal to the perpendicular insufflation vent holes 12. The flapper valve 55 in one aspect is a single-piece component with a hinged flapper door. The flapper door remains closed during traversal of the obturator across a body wall to prevent the ingress of moisture and body fluids into the distal tip of the obturator from the vent holes 12. Under pressure from the insufflation gas, the flapper door opens enabling the insufflation gas to flow into the body cavity.

Figure 31:
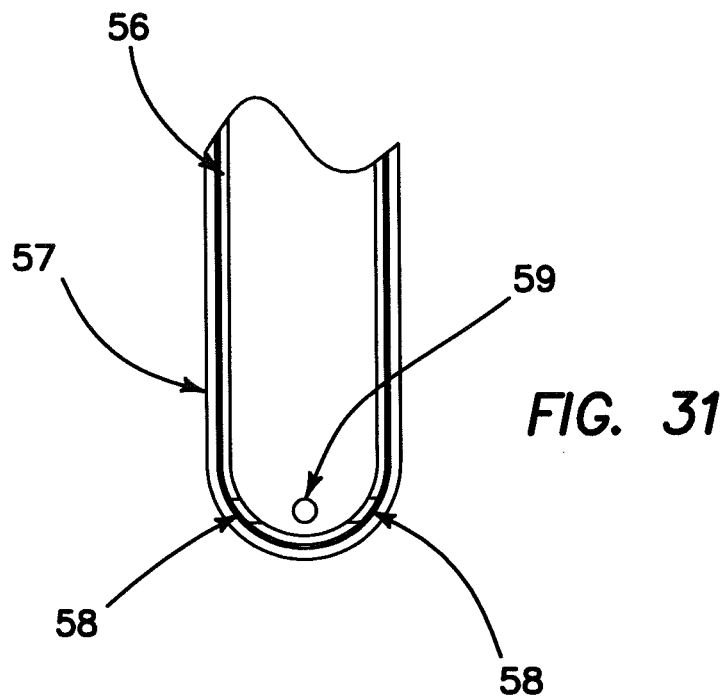
Figure 32:
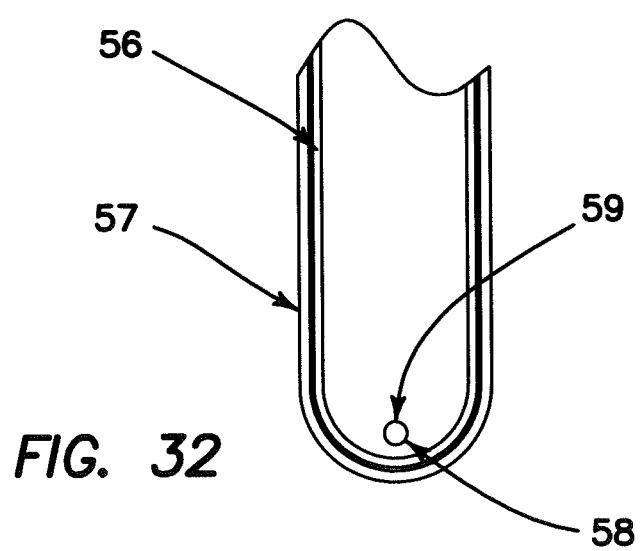

As shown in FIGS. 31-32, the obturator in one aspect has longitudinal and/or concentric inner and outer tubes 56,57 where the inner tube 56 rotates freely within the outer tube 57 about a central axis of the obturator. Both the inner tube 56 and the outer tube 57 have insufflation vent holes 58,59. During traversal across a body wall, the inner tube 56 is rotationally positioned such that the vent holes 58 in the inner tube 56 are not aligned with the vent holes 59 in the outer tube 57 thus creating a sealed condition to prevent the ingress of moisture and body fluids into the tip 7 of the obturator. Upon entry into the body cavity, the inner tube 56 is rotated such that the vent holes 58 on the inner tube are aligned with the vent holes 59 on the outer tube 57 allowing the flow of insufflation gas through the vent holes 58,59 and into the body cavity. The inner tube 56 and/or the outer tube 57 in one aspect are injection molded of transparent polycarbonate materials.

Figure 33:
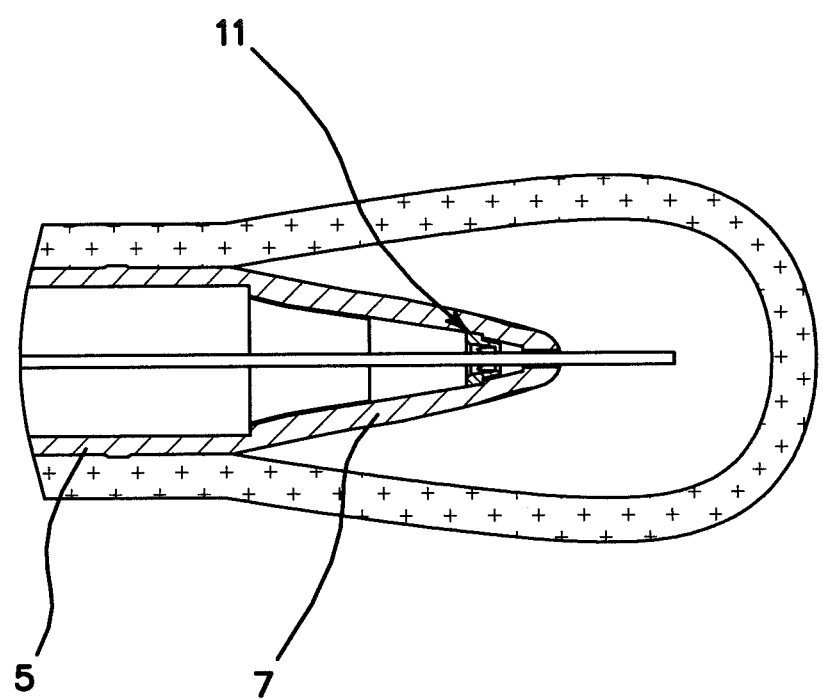

Referring now to FIG. 33, the obturator shaft 5 is formed of a flexible material with a rigid or semi-rigid tip 7, arranged in one aspect to be used with a flexible scope, and without a cannula 20 to visually gain access to an area within a body including but not limited to a body conduit, a body cavity, a body organ, and a body wall. The obturator in one aspect has a longitudinal vent hole 12' in the tip 7 with the micro-seal, e.g., duckbill valve, positioned proximal to the vent hole in the tip of the obturator. The micro-seal prevents the ingress of moisture, body tissue, and body fluids enabling precise visual placement of the tip 7 of the obturator into a targeted area. Once the obturator is properly positioned within the body, the area surrounding the obturator is insufflated with an insufflation gas to facilitate access to the targeted area. Another device can be inserted into a working channel of the obturator to conduct a surgical procedure such as brachytherapy or a breast biopsy. The surgical procedure, such as a breast biopsy, could be completed with or without visualization. The obturator could also include other types of internal micro-seals such as flapper valves or disc type valves. The internal micro-seal acting as a zero seal could also include a septum or instrument seal to seal around inserted instruments.

In one aspect, as the obturator traverses body tissue, pressurized insufflation gas are utilized to separate or dissect tissue away from the tip 7 of the obturator 5 thus lowering the force required to traverse the body tissue. The insufflation gas flows through the distal insufflation vent holes in the obturator 5 and into the body tissue forcing the body tissue away from the obturator tip 7. The insufflation gas is also used to separate relatively soft body tissue to enable access to a targeted body area within a relatively confined space. The obturator 5 in one aspect is formed of either a flexible material or a rigid material and used with or without a cannula 20.

In especially tortuous body conduits or surgical access pathways, the micro-seal preventing the ingress of fluid and/or tissue, e.g., fat, provides the ability to leave the laparoscope inserted into the obturator as it travels the pathway, thereby enhancing accuracy in movement of the obturator and access to the surgical site. As such, removal of the laparoscope to clean and/or de-fog the scope is avoided. Also, it may not be feasible, to subsequently re-enter the laparoscope and obturator into the body conduit after removal of the laparoscope.

Figure 34:
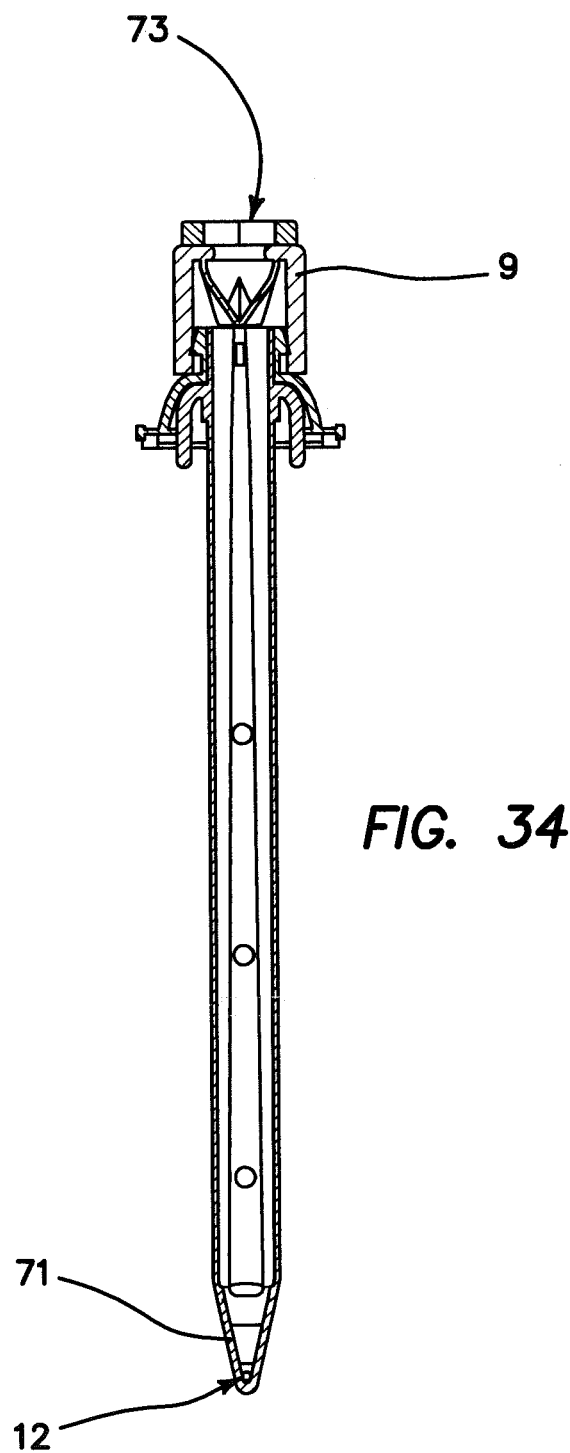
FIG. 34 is a cross-sectional view of an obturator in accordance with various aspects of the present invention.

As shown in FIG. 34, the inside wall 71 of the tip 7 of the obturator in one aspect is coated with an anti-fog solution to prevent excessive moisture from collecting on the inner wall of the obturator and to assist in maintaining optimal visibility through the tip of the obturator. The anti-fog solution is used with or without a valve in the tip of the obturator. In one aspect, a valve in the tip of the obturator is replaced with two perpendicular vent holes 12 in the tip 7 of the obturator. The anti-fog solution is applied via a dipping or coating process and then allowed to dry. Upon exposure to moisture, the anti-fog agent activates thereby preventing condensation from collecting on the inside walls 71 of the obturator. The anti-fog solution in one aspect is formulated from a mixture of 1% by weight docusate sodium and 99% by weight distilled water.

The laparoscope seal 9 in one aspect is coated with an anti-fog solution such that as the laparoscope passes through the laparoscope seal, the lens of the laparoscope is coated with the anti-fog solution. Once the laparoscope lens is coated with the anti-fog solution, condensation will not form on the laparoscope lens or is greatly minimized thereby maintaining optimal visibility during traversal of the obturator across a body wall. In one aspect, the laparoscope seal comprises an insert, pad or cap 73 saturated with an anti-fog solution. The insert 73 of the laparoscope seal 9 in one aspect is a form with a single slit, a plurality of slits, an aperture, or a combination thereof defining a passageway for the laparoscope through the foam. As the laparoscope is inserted into the obturator, the laparoscope passes through the saturated foam 73 thereby coating the lens of the laparoscope with the anti-fog solution. Once the lens of the laparoscope is coated with the anti-fog solution, condensation will not form on the laparoscope lens or is greatly minimized thereby maintaining optimal visibility during traversal of the obturator across a body wall. In one aspect, one or more applicators, e.g., foam or gel rollers or cylinders, saturated with anti-fog solution, is positioned within the handle of the obturator, such that as the laparoscope passes through the applicator coats the lens of the laparoscope with anti-fog solution.

The insert, pad or cap 73 in one aspect is formed, entirely or partially, from various materials such as silicone foam, polyurethane foam, polyethylene foam, ethylene vinyl acetate foam, PVC foam, felt, and cotton. The saturated cap in one aspect is bonded to the proximal end of the obturator and/or the proximal end of the laparoscope seal. To prevent evaporation of the anti-fog solution, the obturator in one aspect is packaged in a non-breathable package such as a mylar pouch or a foil pouch, both of which could be sterilized via gamma radiation sterilization or electron beam sterilization. The cap 73 in one aspect can also be contained within a sealed section of the obturator to prevent migration of the anti-fog solution from the cap.

Figure 35:
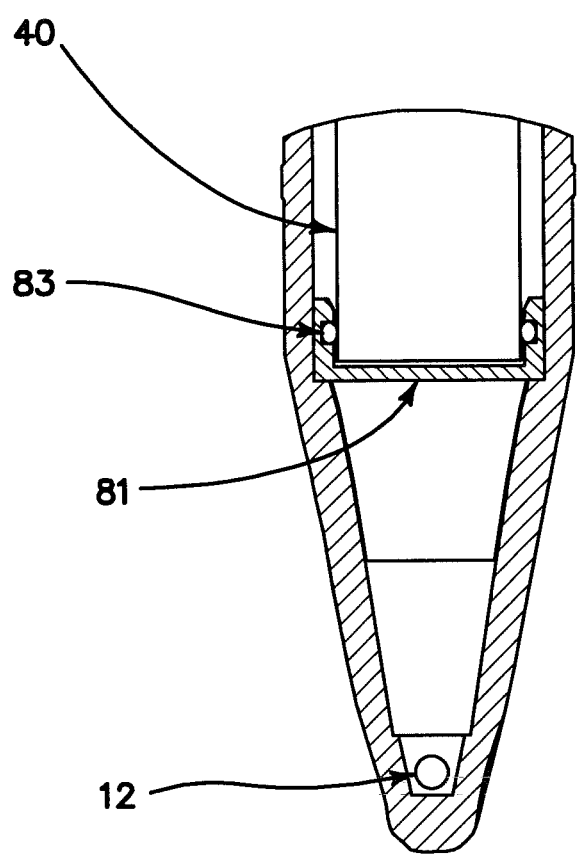
FIGS. 35-37 are cross-sectional views of various tips of an obturator in accordance with various aspects of the present invention.

In FIG. 35, the obturator in one aspect has a transparent lens 81 fitted adjacent to or into the tip 7 of the obturator that includes an internal elastomeric seal 83 configured to seal around the outside diameter of the laparoscope. The lens 81 encases the tip of the laparoscope to prevent fogging of the laparoscope. The lens 81 and/or the elastomeric seal 83 in one aspect is arranged to have a relatively close fit with the outside diameter of the laparoscope 40 to minimize the flow of moisture into the space between the lens 81 and the distal tip of the laparoscope. The lens in one aspect is also coated with an anti-fog solution to prevent condensation from collecting on the lens. The lens 81 in one aspect is shaped to provide additional magnification of the image. The additional magnification of the image provided by the lens enhances the visibility of the surrounding tissue during traversal of the obturator 10 across a body wall. The thickness of the lens 81 in one aspect ranges from about 0.001" to about 0.250". The lens 81 in one aspect is formed from various transparent materials including glass, infrared absorbent glass, polycarbonate, acrylic, polyvinyl chloride, PET, PETE, PETG, cellophane, silicone, polyurethane, polyetherimide, polyamide, and polysulfone. In one aspect, the lens 81 is positioned such that the lens does not obstruct the insufflation pathway through the elongate body and out the aperture in the tip. In one aspect, an insufflation channel parallel with the longitudinal axis of the elongate body assists in providing a pathway around the lens extending across the tip cavity and out through the aperture in the tip.

Figure 36:
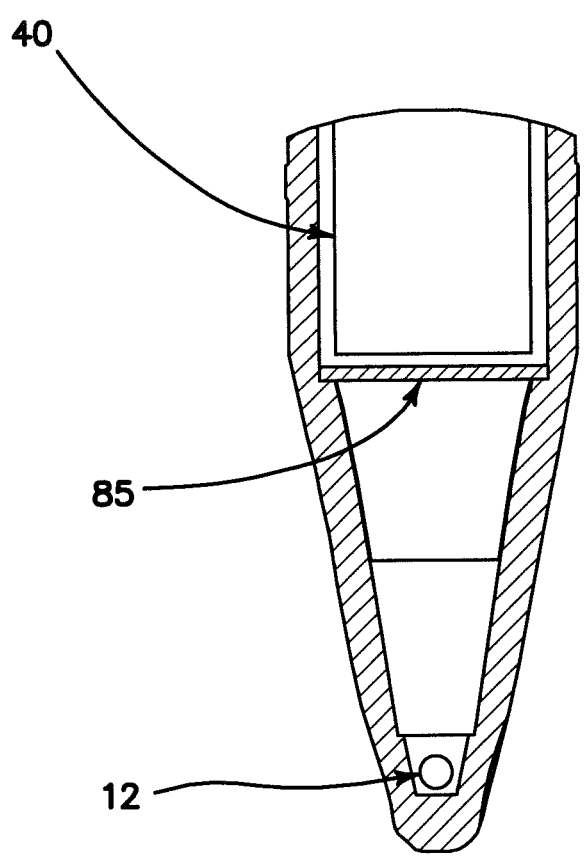

Referring now to FIG. 36, the obturator 10 in one aspect has a transparent disc lens 85 fitted into the tip 7 of the obturator 10. The distal end of the laparoscope 40 is juxtaposed to the disc lens 85. Heat generated by the light from the laparoscope serves to heat the polycarbonate disc lens 85, which in turn heats the lens of the laparoscope 40 to prevent condensation from forming on the lens of the laparoscope 40. The disc lens 85 in one aspect is coated with an anti-fog solution to prevent condensation from forming on the lens 85. The thickness of the lens 85 in one aspect ranges from about 0.001" to about 0.250". The lens 85 in one aspect is formed from various transparent materials such as glass, infrared absorbent glass, polycarbonate, acrylic, polyvinyl chloride, PET, PETE, PETG, cellophane, silicone, polyurethane, polyetherimide, polyamide, and polysulfone.

Figure 37:
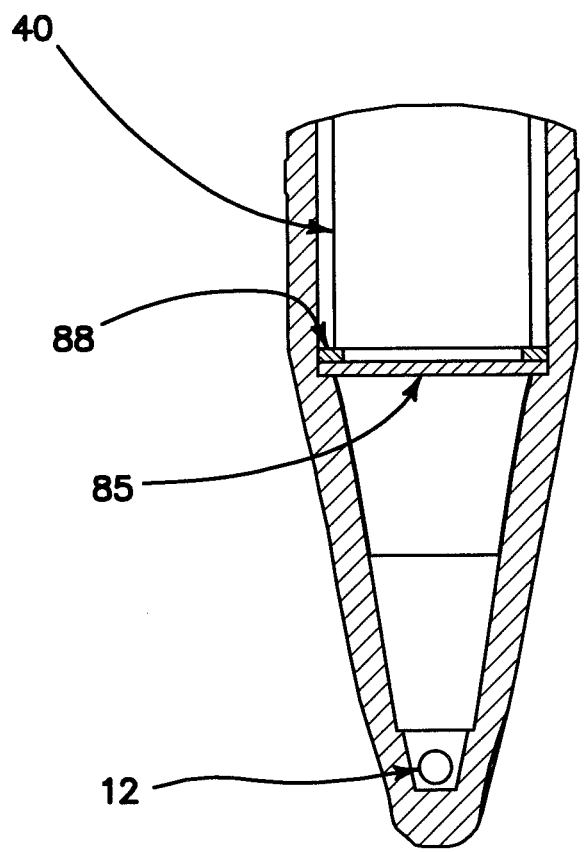

In FIG. 37, in one aspect, the obturator has a transparent disc lens 85 as described above with an elastomeric perimeter seal 88 loosely positioned on the proximal side of the lens. The seal in one aspect is arranged as an o-ring or a planar type seal and serves to create a seal between the distal end of the laparoscope and the proximal face or side of the disc lens 85. The seal 88 prevents body moisture from contacting the lens of the laparoscope 40 and therefore prevents condensation from collecting on the laparoscope lens. The disc lens 85 in one aspect is coated with an anti-fog solution to prevent condensation from collecting on the surfaces of the disc lens 85. The elastomeric perimeter seal 88 in one aspect is formed from various materials such as polyisoprene, silicone, urethane, ethylene propylene diene monomer, Kraton®, nitrile, neoprene, or various closed cell foam materials. The elastomeric perimeter seal 88 in one aspect is adhered to the disc lens 85 through an overmolding process. The elastomeric perimeter seal 88 in one aspect is bonded to the disc lens 85 with an adhesive.

Accordingly, the present invention provides a visual insufflation port/obturator. Although this invention has been described in certain specific embodiments, many additional modifications and variations would be apparent to those skilled in the art. It is therefore to be understood that this invention may be practiced otherwise than specifically described, including various changes in the size, shape and materials, without departing from the scope and spirit of the present invention. Thus, embodiments of the present invention should be considered in all respects as illustrative and not restrictive, the scope of the present invention to be determined by the appended claims and their equivalents rather than the foregoing description.

We claim:

1. A surgical access device comprising an insufflation obturator comprising:
    an elongate body having a longitudinal axis, a proximal end, a distal end and a body lumen extending from the proximal end of the elongate body to the distal end of the elongate body;
    a handle connected to the proximal end of the elongate body;
    a bladeless, tapered tip at the distal end of the elongate body and having a tip cavity, the tip cavity being interconnected with the body lumen; the tip having an inner surface and an outer surface defining a tip wall; the tip including an insufflation vent hole extending across the tip wall through the outer surface and the inner surface and into the tip cavity interconnecting the tip cavity with outside of the tip; the tip including an aperture extending across the tip wall through the outer surface and the inner surface and into the tip cavity interconnecting the tip cavity with outside of the tip; the aperture being coaxial with the longitudinal axis;
    an insufflation gas pathway defined from the proximal end of the elongate body and out through the vent hole for the delivery of insufflation gas; and
    a micro-seal located inside the aperture and adjacent to the vent hole such that the micro-seal is partially resident inside the tip cavity and partially resident outside the obturator and configured such that the entire micro-seal is movable with respect to the tip between a first position sealing the vent hole and a second position permitting insufflation gas to flow out through the vent hole.

2. The surgical access device of claim 1 wherein the micro-seal is in the first position and pressurization of the obturator by delivery of insufflation gas into the insufflation gas pathway moves the micro-seal into the second position.

3. The surgical access device of claim 1 wherein the micro-seal includes an o-ring or an elastomeric seal at its proximal end to assist in sealing the micro-seal with the inner surface.

4. The surgical access device of claim 1 wherein the micro-seal is elongate with an enlarged distal end.

5. The surgical access device of claim 1 wherein vent hole has a longitudinal axis that is substantially perpendicular to the longitudinal axis of the elongate body.

6. The surgical access device of claim 1 further including a cannula having a proximal end, a distal end and a central lumen configured for receiving the obturator; the elongate body and tip movable into the cannula with the handle extending away from the proximal end of the cannula and the tip extending through the distal end of the cannula.

7. The surgical access device of claim 1 wherein the tip is transparent.

8. The surgical access device of claim 1 wherein when in the second position, the micro-seal is distal relative to when the micro-seal is in the first position.

9. The surgical access device of claim 8 wherein the obturator is configured such that during traversal across a body wall by the tip, the body wall provides a compressive force on the micro-seal moving it proximally to a proximal the first position covering and sealing the vent hole.

10. The surgical access device of claim 1 wherein the micro-seal is elongate with an enlarged distal end; the enlarged distal end being resident outside the obturator.

11. The surgical access device of claim 1 wherein during pressurization of the obturator with insufflation gas, the micro-seal is forced to the second position.

12. The surgical access device of claim 1 wherein the vent hole wherein the vent hole and the micro-seal are positioned close to a most distal portion of the tip to prevent interference with a viewing path of a laparoscope inserted inside the body lumen.

13. A surgical access device comprising an insufflation obturator comprising:
    an elongate body having a longitudinal axis, a proximal end, a distal end and a body lumen extending from the proximal end of the elongate body to the distal end of the elongate body;
    a handle connected to the proximal end of the elongate body;
    a bladeless, tapered tip at the distal end of the elongate body and having a tip cavity, the tip cavity being interconnected with the body lumen; the tip having an inner surface and an outer surface defining a tip wall; the tip including an insufflation vent hole extending across the tip wall through the outer surface and the inner surface and into the tip cavity interconnecting the tip cavity with outside of the tip;
    an insufflation gas pathway defined from the proximal end of the elongate body and out through the vent hole for the delivery of insufflation gas; and
    a micro-seal located adjacent to the vent hole and internal in the tapered tip; the micro-seal comprising a piston disposed in a cylinder and configured such that the piston is movable with respect to the tip between a first position sealing the vent hole and a second position permitting insufflation gas to flow out through the vent hole;
    wherein the vent hole is perpendicular to the longitudinal axis.

14. The surgical access device of claim 13 wherein the micro-seal further includes a spring disposed inside the cylinder and configured to bias the piston in the first position.

15. The surgical access device of claim 13 wherein when in the second position, the micro-seal is distal relative to when the micro-seal is in the first position.

16. The surgical access device of claim 13 wherein the micro-seal is adjacent the vent hole such that the piston covers the vent hole in the first position.

17. The surgical access device of claim 13 wherein the tip and the piston are made of transparent material.

18. The surgical access device of claim 13 wherein the piston prevents moisture or fluid from flowing into the tip when in the first position.

19. The surgical access device of claim 13
    wherein the vent hole and the micro-seal are positioned close to a most distal portion of the tip to prevent interference with a viewing path of a laparoscope inserted inside the body lumen.

* * * * *